US008642502B2

(12) United States Patent
Gorkovenko

(10) Patent No.: US 8,642,502 B2
(45) Date of Patent: Feb. 4, 2014

(54) REVERSIBLE GEL-FORMING COMPOSITIONS FOR CONTROLLED DELIVERY OF BIOACTIVE SUBSTANCES

(75) Inventor: Alexander A. Gorkovenko, Mission Viejo, CA (US)

(73) Assignee: TRGel, LLC, Mission Viejo, CA (US)

( * ) Notice: Subject to any disclaimer, the term of this patent is extended or adjusted under 35 U.S.C. 154(b) by 303 days.

(21) Appl. No.: 13/270,144

(22) Filed: Oct. 10, 2011

(65) Prior Publication Data

US 2012/0087891 A1     Apr. 12, 2012

Related U.S. Application Data

(60) Provisional application No. 61/391,681, filed on Oct. 11, 2010.

(51) Int. Cl.
*B01J 20/26*     (2006.01)
(52) U.S. Cl.
USPC .......................................... 502/402; 502/526
(58) Field of Classification Search
USPC ................................................ 502/402, 526
See application file for complete search history.

(56) References Cited

U.S. PATENT DOCUMENTS 5,702,717 A     12/1997     Cha et al.

FOREIGN PATENT DOCUMENTS

| JP | 02078629 | 3/1990 |
| WO | WO 98/02142 | 1/1998 |

OTHER PUBLICATIONS

Martini et al. In J. Chem. Soc., 90(13): 1961-1966 (1994).
Berman et al., Polymer Science U.S.S.R., vol. 30, No. 3, pp. 481-487, 1988 (Permagon Press).
Berman et al, Polymer Science U.S.S.R., vol. 30, No. 2, pp. 394-400, 1988 (Permagon Press).
Berman et al., Bioorganischeskaya Khimiya, vol. 11, No. 8, pp. 1125-1129, 1985 (Plenum Publishing corp.).

*Primary Examiner* — Edward Johnson
(74) *Attorney, Agent, or Firm* — Gary L. Loomis; G.L.Loomis & Assoc., Inc.

(57) ABSTRACT

The present invention relates biomedically useful compositions containing bioactive agents and biodegradable carbohydrate polyethers that exhibit reverse thermogelation properties in aqueous media. The microstructure structure and properties of the carbohydrate polyethers can be conveniently controlled with respect to functionality, molecular weight, polydispersity index, microstructure and tertiary structure, they can be customized for use in a variety of biomedical applications including drug delivery, cell delivery, surgical procedures and the like.

21 Claims, 6 Drawing Sheets

REVERSIBLE GEL-FORMING COMPOSITIONS FOR CONTROLLED DELIVERY OF BIOACTIVE SUBSTANCES

CROSS-REFERENCE TO RELATED APPLICATION

This application claims priority under 35 U.S.C. §119(e) to U.S. Provisional Application No. 61/391,681 filed Oct. 11, 2010, which is herein incorporated by reference.

FIELD OF THE INVENTION

The present invention relates to reverse thermogel carbohydrate polyether compositions in biomedical applications. More specifically the invention relates to controlled release of bioactive substances from such compositions within a mammalian body.

BACKGROUND

Many bioactive materials such as drugs have only limited solubility and/or stability in conventional liquid carriers and are therefore difficult to formulate and administer. In many cases, numerous administrations are required to achieve a desired therapeutic effect over an extended period of time. Various dosage forms and polymeric drug delivery devices and have been investigated for long term, therapeutic treatment of various diseases.

Certain polymers exhibit abrupt changes in aqueous solubility as a function of temperature. Certain of such polymers exhibit a lower critical solution temperature (LCST), wherein the interactive forces (e.g. hydrogen bonding) between water molecules and polymer molecules become unfavorable and phase separation occurs. Consequently, aqueous solutions of such polymers often display relatively low viscosity at ambient temperature and exhibit a sharp increase in viscosity following a small temperature increase, resulting in formation of a semi-solid gel. In certain polymers such a transition from a relatively low viscosity solution to a semi solid hydrogel occurs within in the range of mammalian body temperatures and therefore biodegradable embodiments of thermogelling (RTG) polymers have been investigated for use in a variety of biomedical applications such as drug delivery, tissue engineering, and wound healing. In such systems pharmaceutical agents are combined with an aqueous polymer solution at low temperature and, upon injection into a mammalian body, a hydrogel is formed such that the pharmaceutical agent can be released in a controlled manner. However, many of the RTG polymers examined to date have serious drawbacks when used in biomedical applications. Certain biodegradable polymers with reverse thermo gelling properties have been investigated in biomedical applications such as drug delivery, tissue engineering, and wound healing; wherein bioactive materials such as small molecule drugs, proteins or stem cells are mixed with the aqueous polymer solution at low temperature and subsequently form a semi-solid hydrogel upon introduction into a mammalian body.

Japanese Patent JP02078629 to Okada et al. (abstract) describes biodegradable block copolymers synthesized by transesterification of poly(lactic acid) (PLA) or poly(lactic acid)/glycolic acid (PLA/GA) and poly(ethylene glycol) (PEG). The resultant product was miscible with water and formed a hydrogel.

U.S. Pat. No. 5,702,717 to Cha et al. describes systems for parenteral delivery of a drug comprising an injectable biodegradable block copolymer-based drug delivery liquid having reverse thermal gelation properties. The systems thus described utilize a hydrophobic polymer block comprising a member selected from the group consisting of poly($\alpha$-hydroxy acids) and poly(ethylene carbonates) and a hydrophilic polymer block comprising polyethylene glycol (PEG). However, since most of the disclosed hydrogels have lower critical solution temperature (LCST) greater than 37° C. such compositions are unsuitable for most biomedical applications.

Martini et al. in J. Chem. Soc., 90(13): 1961-1966 (1994) describe low molecular weight ABA type triblock copolymers which utilize blocks of hydrophobic poly($\epsilon$-caprolactone) and blocks of hydrophilic polyethylene glycol. However, the in vitro degradation slow degradation rates for such copolymers greatly limits their use in sustained-release systems.

Thermosensitive water-soluble biodegradable polymers comprising polylactic acid (PLA) or polylactic acid/polyglycolic acid (PLA/PGA) blocks have been widely investigated for use in biomedical applications. However such compositions are known to generate lactic acid and glycolic acid upon biodegradation, wherein such acids may have adverse effects on acid sensitive drugs. Furthermore, such biodegradable polymers have limited stability when stored in aqueous solution.

Stratton et al., in WO 98/02142 describe compositions comprising polyoxyethylene-polyoxypropylene block copolymers (sold commercially under the trade name Pluronics®) having RTG properties for the delivery of proteins. However, such materials have limited use in biomedical applications since they are toxic to body organs and are non-biodegradable. Moreover, only high molecular weight polyoxyethylene-polyoxypropylene block copolymers at higher concentrations (15-25 wt. %) exhibit RTG properties.

Other known thermosensitive polymers include poly(ethylene oxide)/polypeptide conjugates and pH-sensitive chitosan/glycerol phosphate compositions. While the degradation products of polypeptides are neutral amino acids and there is no significant pH drop during polymer degradation, such polymers are usually difficult to reproducibly synthesize; and chitosan/glycerol phosphate compositions are known to have low MW components, which may diffuse from the gel causing phase separation of pH sensitive chitosan molecules. In general, natural polymers are much less desirable than synthetic polymers because of batch-to-batch properties variation.

Still other known thermosensitive polymers include water-soluble polyphosphazenes. However, such polyphosphazenes have limited utility since they are not readily biodegradable. While such water-soluble poly(phosphazenes) have been studied for drug delivery applications, storage time in aqueous solutions is limited by slow hydrolysis.

Therefore there exists a need for injectable thermosensitive biodegradable hydrogels materials that may prepared by methods that allow for a high degree of control of all molecular, chemical and physical properties.

There exists another need for method for reproducibly providing carbohydrate, non-polysaccharide based materials with control of relative hydrophilicity/hydrophobicity.

There exists yet another need for thermogelling materials that may be conveniently modified or custom synthesized to accommodate the degradation rate, sol-gel transition temperature, critical gelation concentration, and permeability for specific applications requirements.

The present invention addresses these and other needs.

SUMMARY OF THE INVENTION

The present invention relates generally to thermosensitive water soluble synthetic carbohydrate polymers used as a component of an injectable drug delivering system and other biomedical applications including stem cell therapy delivery system to avoid spreading of the cells in the host after initial introduction, stem cell preservation solution/gel, articular cavity injection, treatment of aneurism (filling of aneurism cavities, etc.), usage for contraception (gelling after introduction as a liquid), scar removal, cosmetic subcutaneous wrinkles/skin defect filling, filling age related facial hollows, lip augmentation, orbital troughs filling (under and around the eye), reduction of folds, preventing people from overeating (additive to cold food) and other applications that require water soluble biocompatible polymer and its gelling or precipitation as a response to a temperature change and injectable thermosensitive biodegradable hydrogels using the same.

The invention relates, more specifically, to polymers of poly(2-3)-1,6-anhydroglucopyranoses and derivatives thereof having controlled weight-average molecular weights, narrow polydispersity indices, controlled microstructure, controlled tertiary structure, controlled glass transition temperature, and controlled hydrophilicity or hydrophobicity and utility as biocompatible injectable thermosensitive biodegradable molecules.

Suitable poly(2-3)-1,6-anhydroglucopyranoses are prepared by an anionic ring-opening living polymerization of 1,6:2,3-dianhydrohexopyranoses (Cerny epoxides) by known methods. Since the resulting 2-3 linked carbohydrate polyethers do not have glycosidic bonding between monomer units, such carbohydrate polyethers are not polysaccharides. Such synthetic polyether carbohydrates can exhibit a polydispersity index (PDI) considerably less than 2.0, which is considerably lower than the PDI for nearly all carbohydrate polymers found in nature as well as most man-made polymers. Furthermore, the chain length of such polymers is readily controlled and may be manipulated to serve the needs of specific applications. Additionally, the synthetic carbohydrate polyethers of the present invention produced via anionic living polymerization techniques are useful in the production of a variety of derivatives with carefully controlled molecular structures.

The present invention also provides compositions and formulations comprising synthetic carbohydrate polyethers with large degree of structural variation achieved by choice of substituents in the 1,6:2,3-dianhydrohexopyranoses monomers as well as by post-polymerization functionalization.

Since the synthetic, non-polysaccharide, carbohydrate polyethers useful in compositions and formulations of the present invention are essentially monodisperse and uniform in structure, the thermo gelling formulations produced there from are consistent with potentially little or no batch-to-batch variability.

The invention presents biodegradable water-soluble non-polysaccharide poly(2-3)-1,6-anhydroglucopyranose compositions and derivatives thereof, which find utility in biocompatible thermosensitive aqueous solutions, wherein certain of such solutions are injectable. Particularly useful synthetic carbohydrate polymers of the present invention are thermosensitive, water-soluble, biocompatible polymers that gel or precipitate in response to an increase in temperature, which is a property known as reverse thermogelation (RTG). Certain embodiments of the present invention relate to biocompatible water-soluble carbohydrate polyether compositions that are particularly useful in pharmaceutical and biomedical applications wherein the compositions afford the controlled release of a wide variety of bioactive molecules including drugs and the like.

In general, the biomedically useful compositions of the present invention comprise at least one bioactive agent in combination with a C2-C3 linked polyether of a 1,6:2,3-dianhydrohexopyranose derivative that exhibits reverse thermal gelation properties in aqueous media. Certain preferred compositions exhibit a critical solution temperature from 5° to 74° C., while certain most preferred compositions exhibit a critical solution temperature from 5° to 44° C. Certain preferred RTG polymers have a molecular weight from 2 to 350 kDa and a polydispersity index less than or equal to 1.5. Certain embodiments are useful as physiologic lubricants. Certain other embodiments are useful for augmentation of body tissue in surgical procedures, while other embodiments are useful as biological scaffolds in wound healing and cell-delivery applications. Certain other embodiments are useful for encapsulation of mammalian cells including, but not limited to, stem cells, islets cells, fibroblast cells, T-cells, B-cells, dendritic cells, osteoblasts, adipose cells, neuronal cells, epithelial cells, smooth muscle sells, liver cells and the like. In certain embodiments the bioactive agent includes, but is not limited to, receptors, hormones, cytokines, hematopoietic factors, growth factors, anti-obesity factors, trophic factors, anti-inflammatory factors, small molecule drugs, nucleic acids, polypeptides, enzymes and the like. In certain embodiments the bioactive agent comprises at least one small molecule drug including, but not limited to, antibiotics, antivirals, antifungals, antineoplastics, antigeogenics, antiarrhythmics, anticoagulants, antihistamines, antihypertensives, antipsychotics, sedatives, contraceptives, decongestants, diuretics, immunosurpressants and the like. In certain embodiments the bioactive agent comprises polypeptides including, but not limited to, oxytocin, vasopressin, adrenocorticotropic hormone, epidermal growth factor, platelet-derived growth factor, prolactin, luliberin, growth hormone, growth hormone releasing factor, insulin, somatostatin, glucagon, interleukin-2, interferon-α, interferon-β, interferon-γ, gastrin, tetragastrin, pentagastrin, urogastrone, secretin, calcitonin, enkephalins, endorphins, angiotensins, thyrotropin releasing hormone, tumor necrosis factor, nerve growth factor, granulocyte-colony stimulating factor, granulocyte macrophage-colony stimulating factor, macrophage-colony stimulating factor, heparinase, bone morphogenic protein, hANP, glucagon-like peptide, interleukin-11, renin, bradykinin, bacitracins, polymyxins, colistins, tyrocidine, gramicidins, cyclosporine, enzymes, cytokines, monoclonal antibodies. vaccines and the like. In certain embodiments the bioactive agent comprises one or more salts and/or buffer compositions. In certain preferred embodiments the biomedically useful composition is effective in removing wrinkles on human skin.

DETAILED DESCRIPTION OF THE INVENTION

Figure 1:
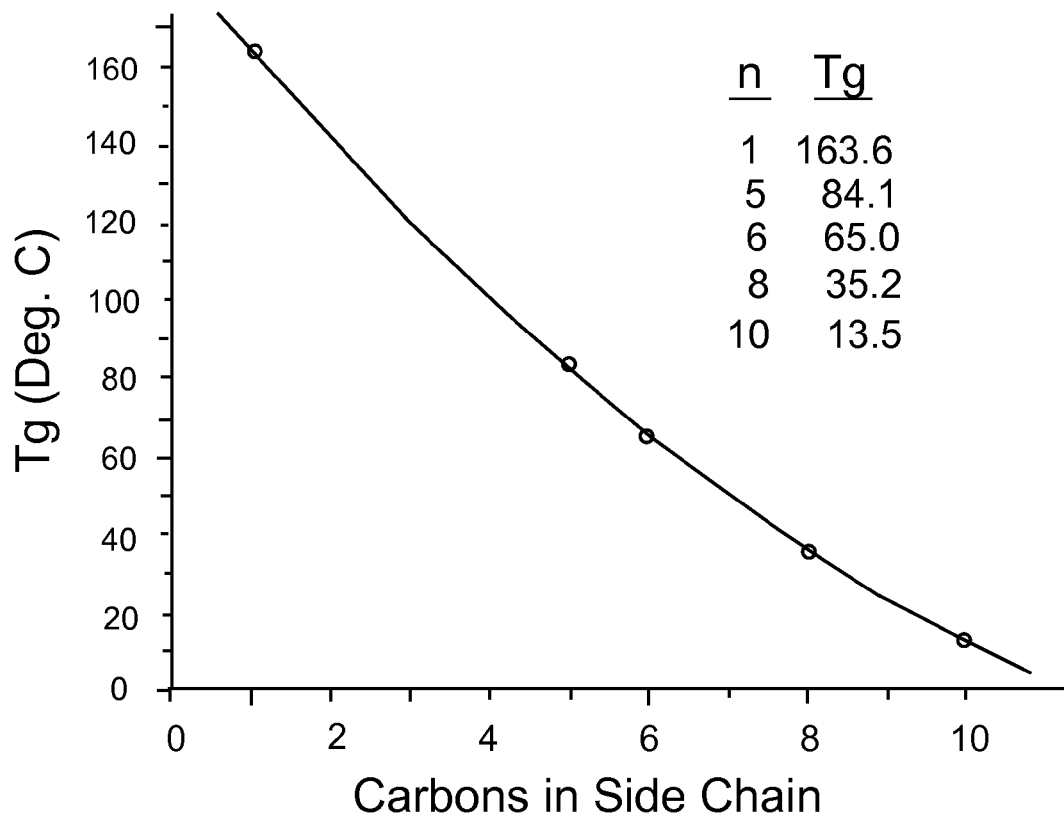
FIG. 1 presents a graph showing relationship between of Tg and number of carbon atoms in an alkyl side-chain of poly(2-3)-1,6-anhydro-4-O-alkyl-β-D-glucopyranose.

As used herein, the following terms shall have the following meaning:

"Reverse thermal gelation (RTG)" is defined as meaning the temperature below which a polymer is soluble in water and above which the polymer forms a semi-solid, i.e. gels, emulsions, dispersions and suspensions.

"Reverse thermogelling polymers" or "RTG polymers" is defined as meaning that the polymer is soluble in water and is capable of reverse thermal gelation.

"LCST", or lower critical solution temperature, is defined as meaning the temperature at which a biodegradable block copolymer undergoes reverse thermal gelation. For purposes of the present invention, the term "LCST" can be used interchangeably with "reverse thermal gelation temperature".

"swellable polymer" refers to a polymer which can absorb at least 1-3% w/w of water without dissolution in an aqueous solution.

"TRGel polymers" refers to poly(2-3)-1,6-anhydro-β-D-glucopyranoses which are soluble in or swell in aqueous media.

"biodegradable" is defined as meaning a material that erodes or otherwise degrades in vivo to afford smaller non-toxic components that may be metabolized or excreted from the body.

"parenteral administration" is defined as meaning any route of administration other than the alimentary canal, including, for example, subcutaneous and intramuscular.

"bioactive agent" is defined as any biologically active material including, but not limited to, medicinal agents, drug, pharmaceutically active compositions, viable cells including, but not limited to, stem cells, islets cells, fibroblast cells, T-cells, B-cells, dendritic cells, and the like, as well as inorganic compositions comprising metal oxides, carbonates, bicarbonates, salts, buffers and the like.

In the monomers designations as used herein: MDM is equivalent to O, MEDM is equivalent to M, DGDM is equivalent to D and 3GDM is equivalent to T.

For the purposes of the present invention a living polymerization is, as defined in the IUPAC Compendium of Chemical Terminology, 2nd Edition, 1997, a chain polymerization from which chain transfer and chain termination steps are absent. In many cases, the rate of chain initiation is fast compared with the rate of chain propagation, so that the number of kinetic-chain carriers is essentially constant throughout the polymerization. In effect, a living polymerization continues until the monomer supply has been exhausted and if additional monomer is added to the reaction mixture the polymerization will resume. Therefore, by variation the monomer feed, block copolymers with well-defined block lengths and very defined random copolymers and terpolymers may be conveniently produced. Polymers of uniform molecular weight, i.e. low polydispersity, are characteristic of polymers produced by living polymerization techniques. Also, since the monomer supply is controllable, the chain length may be manipulated to serve the needs of a specific application. Additionally, anionic living polymerization techniques are useful in the production of a variety of polymers with carefully controlled structures including branched polymers, ladder polymers, framework polymers, star polymers, AB type diblock copolymers and ABA type triblock polymers as well as variations and combinations thereof. The carbohydrate polymer structures made according to anionic living polymerization techniques herein described can be produced with a high degree of regiospecificity, stereospecificity and precisely controlled molecular weight, rendering such polymers ideal for use as TRG materials with precise controlled gelling temperature, gel strength, and biodegradation (in vivo residence time) rates useful for applications cited herein.

Certain polymers useful in embodiments of the present invention are carbohydrate polyethers, which can be linear or non-linear and can be homopolymers, copolymers or combinations thereof. The non-linear polymers of the invention can have a variety of architectures, including for example star-polymers, branched polymers, graft polymers, crosslinked polymers, semi-cross-linked polymers and the like or combinations thereof. These various polymer architectures are achieved with a high degree of control by the polymer preparation methods of the invention.

A particularly desired feature of embodiments of the carbohydrate polyethers of the present invention is that they have a narrow polydispersity index (PDI), which is a measure of the distribution of molecular mass in a given polymer sample. Example of very narrow polydispersity and controlled MW can be found in Tables 1, 2 and 3 of Examples 8, 9, and 10 respectively. The PDI is calculated as the weight average molecular weight (Mw) divided by the number average molecular weight (Mn). Therefore PDI=Mw/Mn and indicates the distribution of individual molecular masses in a given polymer preparation. The PDI always has a value of 1.0 or greater and in a given polymer as the chains approach uniform length the PDI approaches unity. Most polysaccharides and carbohydrate polymers found in nature as well as most man-made polymers have a PDI greater than 2.0 with many having a PDI greater than 5.0. By contrast the polydispersity index (PDI) of the polymers useful in embodiments of the present invention is less than 2.0. The preferred PDI for all polymers useful in embodiments of the present invention is in the range of about 1.05 to 2.0 with a range of about 1.05 to 1.5 being most preferred.

A 1,6:2,3-dianhydrohexopyranose monomer useful for the synthesis of polymers of the present invention is shown in general structural formula (I) wherein R represents any moiety that does not interfere with anionic living polymerization, i.e., R should be a moiety that is weakly reactive or unreactive toward anions and other strong nucleophiles. In general, R is chosen to be a moiety that is neither nucleophilic nor electrophilic. In certain embodiments of the present invention R=straight-chain or branched alkyl, straight-chain or branched alkenyl, aryl, alkyl substituted aryl, aryl substituted alkyl, oxyalkyl, oxyethyl, poly(oxyalkylene), and poly(oxyethyene). In certain preferred embodiments R=straight-chain or branched alkyl with chain lengths from 1 to 18 carbon atoms and straight-chain or branched alkenyl with chain lengths from 1 to 18 carbon atoms. In certain other preferred embodiments R=straight-chain or branched alkyl with chain lengths from 1 to 12 carbon atoms and straight-chain or branched alkenyl with chain lengths from 1 to 12 carbon atoms. Particularly useful monomers for the synthesis of polymers of the present invention are 1,6:2,3-dianhydrohexopyranose monomers of structural formula (I) wherein R=allyl or benzyl.

(I)

(II)

Monomer units of the C2-C3 linked carbohydrate polyethers produced directly by the anionic, ring-opening, living polymerization of a monomer of formula (I) are represented by the general structural formula (II), wherein n=the average number of monomer units in a polymer chain.

The overall synthesis of a poly(2-3)-1,6-anhydro-4-O-β-D-glucopyranose of formula (II) by the anionic, ring-opening polymerization of a 1,6:2,3-dianhydrohexopyranose of formula (I) is illustrated in Reaction Scheme A. In this reaction sequence, the anionic initiator $A^-$ attacks the 1,6:2,3-dianhydrohexopyranose (I) at C-2 opening the 2-3 epoxy ring to afford the alkoxyl anion of formula (III) which subsequently the attacks a second molecule of (I) in a like manner to open the 2-3 epoxy ring forming an ether linkage and a new alkoxyl anion of formula (IV) to begin the living polymerizing chain. This sequence of steps continues until all monomer is consumed and a high polymer is produced. It is important to note that such a living polymerization can be stopped at anytime by starving the reaction mixture of monomer at which time the growing polymer chain has a 'living end' and that the polymerization resumes when new monomer is introduced. The new monomer may be the same as the initial monomer or may be any other suitable monomer. Furthermore, two or more suitable monomers may be present in the initial reaction mixture, wherein the structure of the resulting copolymer is controlled by the concentrations and relative reactivity of the monomers. Since such a living polymerization adds monomers to a growing chain in serial fashion, molecular weight and copolymer composition are precisely controlled. Also, initiation of such living polymerizations can occur heterogeneously, i.e. from suitably reactive surfaces or in networks with suitable reactive sites such as anions.

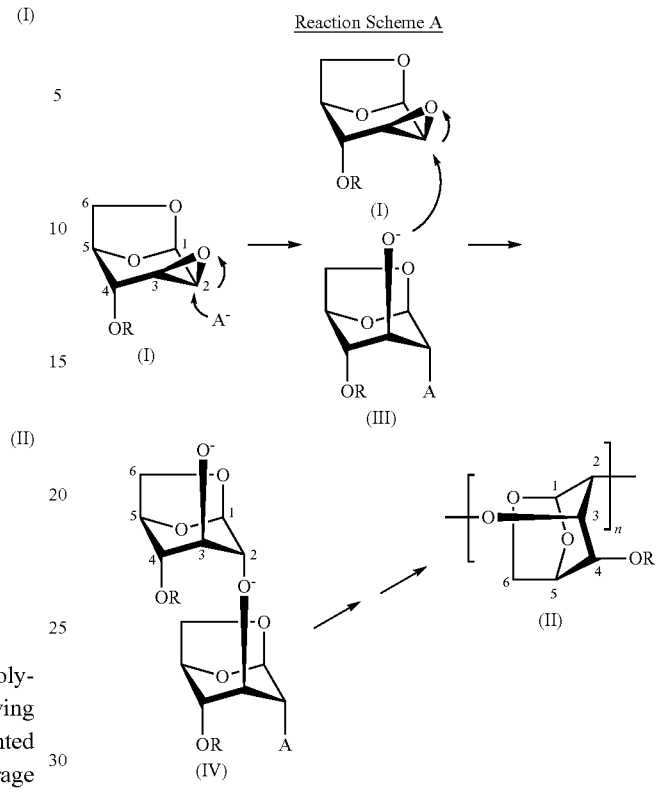

Reaction Scheme A

In certain embodiments, after polymerization any or all of the —OR functionalities attached to C-4 of the carbohydrate polyethers of general formula (II) are de-protected and/or derivatized to introduce a wide variety of functionality, thus offering a degree of flexibility of structural variation that is not possible with polysaccharides known in the art. In such a post-polymerization functionalized carbohydrate polyether units of general formula (II) the moiety —OR at the C-4 ring position are chosen from or are converted to a variety of reactive functional moieties such as amines, amides, carboxylic acids, esters, aldehydes, ketones, alkylthiols, arylthiols, carbamates, arylates, cyanates, ioscyanates, haloalkanes, haloformates, N-hydroxysuccinimides, maleimides, phosphates, phosphorodithioates, phosphites, phosphonates, phosphorothioates, pyridyldisulphides, sulphamates thiophosphates. silanes, siloxanes, thioethers, nitrates, nitriles, nitrosooxy, thiols, sulfides, disulfides and the like. In certain preferred embodiments of carbohydrate polyethers represented by the general formula (II) R is chosen from the group consisting of H, straight-chain alkyl, branched alkyl, straight-chain alkenyl, branched alkenyl, allyl, aryl, benzyl, carbamyl, N-substituted carbamyl, alkanoyl and aroyl. Particularly useful substituted carbamate moieties including 3,5-dimethylphenylcarbamate, dichlorophenylcarbamates, phenylcarbamates, and tolylcarbamates as well as mixtures thereof.

Certain embodiments utilize copolymers of the general formula (V), wherein n and m represent the number of monomer units per chain. Such copolymers may be random copolymers, block copolymers or combinations of random copolymers and block copolymers.

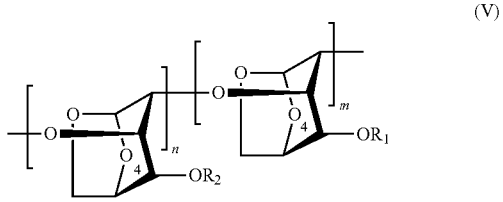

(V)

In such copolymers the moieties —$OR_1$ and —$OR_2$ at the C-4 ring positions are chosen from or are converted to variety of reactive functional moieties such as amines, amides, carboxylic acids, esters, aldehydes, ketones, alkylthiols, arylthiols, carbamates, arylates, cyanates, ioscyanates, haloalkanes, haloformates, N-hydroxysuccinimides, maleimides, phosphates, phosphorodithioates, phosphites, phosphonates, phosphorothioates, pyridyldisulphides, sulphamates thiophosphates. silanes, siloxanes, thioethers, nitrates, nitriles, nitrosooxy, thiols, sulfides, disulfides and the like. In certain preferred embodiments of carbohydrate polyethers represented by the general formula (V) $R_1$ and $R_2$ are chosen from the group consisting of H, straight-chain alkyl, branched alkyl, straight-chain alkenyl, branched alkenyl, allyl, aryl, benzyl, carbamyl, N-substituted carbamyl, alkanoyl and aroyl. Particularly useful substituted carbamate moieties including 3,5-dimethylphenylcarbamate, dichlorophenylcarbamates, phenylcarbamates, and tolylcarbamates as well as mixtures thereof.

Certain preferred embodiments of copolymers of formula (V) comprise 1-5% monomer units wherein $R_1$ or $R_2$=allyl. Such allyl functionalization is particularly useful in providing the polymers with carbon-carbon double bonds as sites for cross-linking.

In certain embodiments, after polymerization any or all of the protected latent hydroxyl functionalities in the C-1, C-4 and C-6 positions of polymers units of the general formula (II) are de-protected and/or derivatized to introduce a wide variety of functionality thus offering a degree of flexibility of structural variation that is not possible with polysaccharides known in the art. Such a functionalized carbohydrate polyether unit is represented by the general formula (VI).

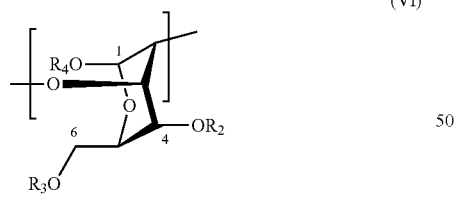

(VI)

In such a functionalized carbohydrate polyether unit represented by the general formula (VI) the moieties —$OR_2$, —$OR_3$ and —$OR_4$ at the C-4, C-6 and C-1 ring positions respectively are chosen from or are converted to variety of reactive functional moieties such as amines, amides, carboxylic acids, esters, aldehydes, ketones, alkylthiols, arylthiols, carbamates, arylates, cyanates, ioscyanates, haloalkanes, haloformates, N-hydroxysuccinimides, maleimides, phosphates, phosphorodithioates, phosphites, phosphonates, phosphorothioates, pyridyldisulphides, sulphamates thiophosphates. silanes, siloxanes, thioethers, nitrates, nitriles, nitrosooxy, thiols, sulfides, disulfides and the like. In certain preferred embodiments of carbohydrate polyethers represented by the general formula (VI) $R_2$, $R_3$ and $R_4$ are chosen from the group consisting of H, straight-chain alkyl, branched alkyl, straight-chain alkenyl, branched alkenyl, allyl, aryl, benzyl, carbamyl, N-substituted carbamyl, alkanoyl and aroyl. Particularly useful substituted carbamate moieties including 3,5-dimethylphenylcarbamate, dichlorophenylcarbamates, phenylcarbamates, and tolylcarbamates as well as mixtures thereof. Additionally in certain other preferred embodiments of carbohydrate polyethers represented by the general formula (VI) the oxygen atoms at C-1, C-4 and C-6 are derivatized by reaction with a polyalkylene ether diol including, but not limited to, polyethylene glycol, polypropylene glycol and poly(tetramethylene ether) glycol. A non-limiting example of a such post polymerization funcionalization is the benzolysis of a monomer unit of a typical carbohydrate polyether of structural formula (II), which leads to a symmetric addition of benzoyl groups to the ring resulting in a polymer in which some or all monomer units have structural formula (VI), where $R_3$=$R_4$=benzoyl. Such a transformation is conveniently effected by stirring polymer with benzoic anhydride in the presence of anhydrous sulfuric acid for a few hours at room temperature.

Another non-limiting example of the post polymerization funcionalization of polymers of the present invention is the acetylation of the oxygen atoms at ring positions C-1 and C-6 of a carbohydrate polyether of structural formula (II), wherein treatment with hydrofluoric acid and acetic anhydride effects a ring opening resulting in introduction of acetyl functionalities, which may further reacted or substituted. Such sequence is illustrated in Reaction Scheme B.

Reaction Scheme B

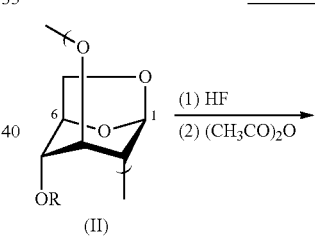

(II)

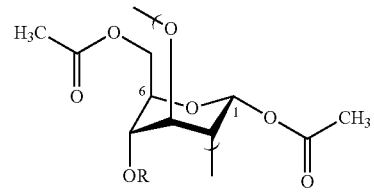

Certain other embodiments of the invention utilize copolymer units of the general formula (VII), wherein n and m represent the number of monomer units per chain. Such copolymers may be random copolymers, block copolymers or combinations of random and block copolymers.

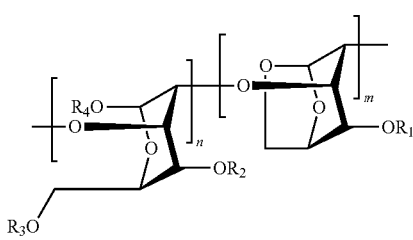

(VII)

In such a functionalized carbohydrate polyether units represented by the general structural formula (VII) the moieties —$OR_1$, —$OR_2$, —$OR_3$ and —$OR_4$ are chosen from or are converted to variety of reactive functional moieties such as amines, amides, carboxylic acids, esters, aldehydes, ketones, alkylthiols, arylthiols, carbamates, arylates, cyanates, ioscyanates, haloalkanes, haloformates, N-hydroxysuccinimides, maleimides, phosphates, phosphorodithioates, phosphites, phosphonates, phosphorothioates, pyridyldisulphides, sulphamates thiophosphates. silanes, siloxanes, thioethers, nitrates, nitriles, nitrosooxy, thiols, sulfides, disulfides and the like. In certain preferred embodiments of carbohydrate polyethers represented by the general formula (VII) the moieties $R_1$, $R_2$, $R_3$ and $R_4$ are chosen from the group consisting of H, straight-chain alkyl, branched alkyl, straight-chain alkenyl, branched alkenyl, allyl, aryl, benzyl, carbamyl, N-substituted carbamyl, alkanoyl and aroyl. Particularly useful substituted carbamate moieties including 3,5-dimethylphenylcarbamate, dichlorophenylcarbamates, phenylcarbamates, and tolylcarbamates as well as mixtures thereof. Additionally in certain other preferred embodiments of carbohydrate polyethers represented by the general formula (VII) the oxygen atoms at C-1, C-4 and C-6 ring positions are derivatized by reaction with a polyalkylene ether diol including, but not limited to, polyethylene glycol, polypropylene glycol and poly(tetramethylene ether) glycol.

In certain embodiments the carbohydrate polyethers of the present invention are designed to be water-soluble, while in certain other embodiments the polymers are designed to be water-insoluble. Additionally, in certain other embodiments the carbohydrate polyethers of the present invention are designed to produce aqueous emulsions, dispersions or suspensions. In essence the relative hydrophilicity/hydrophobicity of the carbohydrate polyethers of the present invention is controlled via selection of the functionality at one or more of the C-1, C-4 and C-6 positions on the glucopyranose rings and the number of rings so functionalized, i.e. the concentration of the functionality. By such selection techniques compositions can be prepared to provide aqueous solutions, aqueous emulsions or aqueous suspensions.

In certain other embodiments 3,5-dimethylphenylcarbamate functionalized polymers are synthesized by treating a polymer of formula II with acetic anhydride and sodium methoxide followed by treatment with an isocyanate as shown in Reaction Scheme C.

Reaction Scheme C

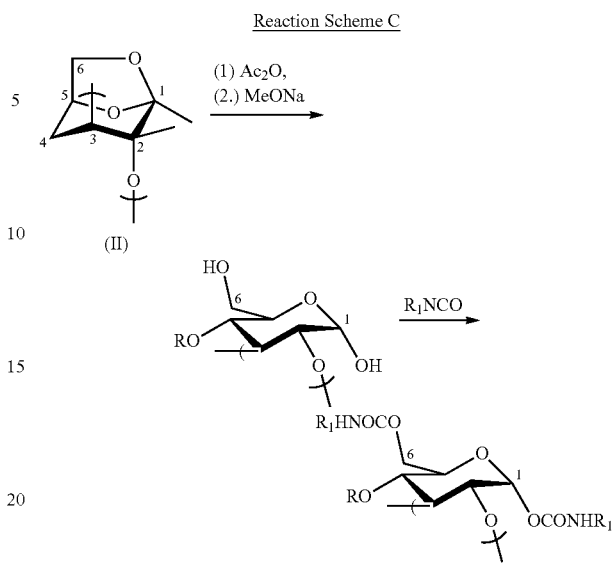

In certain other embodiments some or all of pyranose ether linkages of 1,6:2,3-dianhydrohexopyranoses of the general structural formula (II) are reductively cleaved to afford non-cyclic polyol units within the polymer chains. Chemical reduction at C-1 of ring-opened derivatives of poly(2-3)-D-glucopyranoses can be achieved by with use of known reducing agents including, but not limited to, sodium borohydride and sodium cyanoborohydride. Particularly useful are the poly(2-3)-sorbitols of structural formula (VIII), which are conveniently prepared from the poly(2-3)-1,6-anhydro-4-O-β-D-glucopyranoses (II) as described by Berman et al., Izvestia Academii Nauk USSR, Ser. Khim. No. 3, pp. 705-707, 1988.

Reaction Scheme D

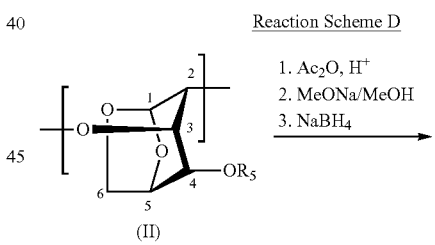

1. $Ac_2O$, $H^+$
2. MeONa/MeOH
3. $NaBH_4$

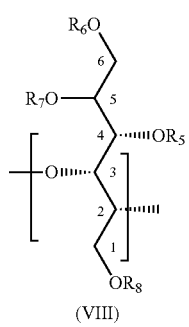

(VIII)

A typical reaction sequence is shown in Reaction Scheme D where in a first step a carbohydrate polyether structural formula (II) is treated with acetic anhydride under conditions of acid catalysis to open the furan ring and introduce acetate moieties at C-1 and C-6. In step 2 the acetate moieties at C-1 and C-6 are saponified with sodium methoxide in methanol to produce C-1 and C-6 hydroxy moieties. Finally, in step 3 reduction of the pyranose ring with sodium borohydride yields the poly(2-3) sorbitols of general structural formula (VIII). These hydroxylated chiral ring-opened derivatives of poly(2-3)-D-glucopyranose may be further derivatized with functionalities known in the art as being suitable for use in biomedical applications. Particularly useful are poly(2-3) sorbitols of general structural formula (VIII) wherein $R_5$, $R_6$, $R_7$ and $R_8$ are chosen from the group consisting of H, straight-chain alkyl, branched alkyl, straight-chain alkenyl, branched alkenyl, allyl, aryl, carbamyl, N-substituted carbamyl, alkanoyl and aroyl. Particularly useful substituted carbamate moieties include 3,5-dimethylphenylcarbamate, dichlorophenylcarbamates, phenylcarbamates, and tolylcarbamates as well as mixtures thereof.

For purposes of the present invention, "water-soluble" is intended to mean that the polymer compositions are substantially soluble in water or other aqueous environments. Thus, although certain regions or segments of a copolymer may be hydrophobic or even water-insoluble, the copolymer molecule, as a whole, dissolves in water or water-containing environments in substantial measure. In general, embodiments of the water-soluble carbohydrate polyethers of the present invention having molecular weight greater than 2,000 Daltons exhibit a water solubility of at least 0.5 g/100 mL, while other embodiments exhibit water solubility of greater than 5 g/100 mL. In yet other embodiments, water-soluble carbohydrate polyethers of the present invention at all molecular weights are completely soluble in or miscible with water or other aqueous compositions. The water-soluble glucopyranose polyethers of the present invention are particularly useful in biological applications such as surface protection from non-specific adsorption.

In certain embodiments, the water-soluble glucopyranose polyethers of the present invention exhibit lower critical solution temperature (LCST) behavior, which means that the polymers are more soluble when the temperature of the solvent is lowered. Other water-soluble polymers such as polyethylene oxide (PEO) also display LCST behavior, but the transition temperature of PEO is about 100° C., while certain embodiments of the water-soluble carbohydrate polyethers of the present invention a transition temperature as low as 30° C. Furthermore, the transition temperature of embodiments of the water-soluble carbohydrate polyethers of the present invention can be modified and controlled via copolymerization and selective functionalization.

Non-limiting examples of embodiments wherein the carbohydrate polyethers of the present invention are water-soluble are presented by structural formula (IX), where p is an integer from 1 to 10, preferably from 1 to 4.

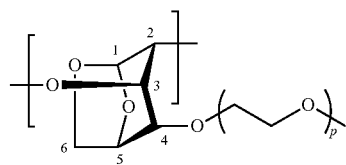

(IX)

Other non-limiting examples of embodiments wherein the carbohydrate polyethers of the present invention are water-soluble are represented by structural formula (VI), wherein at least one of $R_2$, $R_3$ and $R_4$ has the structure:

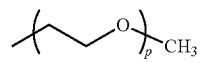

where p is an integer from 1 to 10 and preferably from 1 to 4

In certain other embodiments the glass transition temperature ($T_g$) of the carbohydrate polyethers is controlled over a wide range by variation of the nature and concentration of the glucopyranose ring substituents. For example, the relationship between $T_g$ and the number of carbon atoms in the alkyl side chain of poly(2-3)-1,6-anhydro-4-O-alkyl-β-D-glucopyranoses with structure of formula (II) is illustrated graphically in FIG. 1, wherein the $T_g$ is observed to increase as the number of carbon atoms in the alkyl side-chain is decreased.

Control of the chain structure, i.e. linear, branched, star and the like, is achieved via use of a suitable monofunctional or polyfunctional anionic initiators. A non-limiting illustration of the preparation of a suitable monofunctional anionic initiator is presented in Scheme E wherein a solution of 2-butoxyethanol, also commonly known as cellosolve, in tetrahydrofuran (THF) is treated with an excess of potassium metal to afford potassium 2-butoxyethoxide. A non-limiting illustration of the preparation of a suitable trifunctional anionic initiator is presented in Scheme F wherein a solution of 1,3,5-benzenetrimethanol in THF is treated with an excess of potassium metal to afford potassium 1,3,5-benzenetrimethoxide. In both of these illustrations, the initiator solution thus produced may be stored over potassium metal in a dry box and the initiator concentration in the solution is determined by titration before use.

Reaction Scheme E

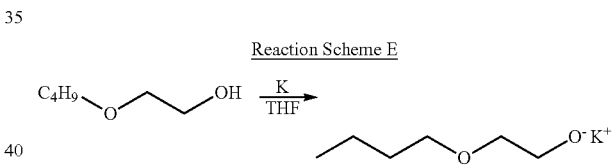

Reaction Scheme F

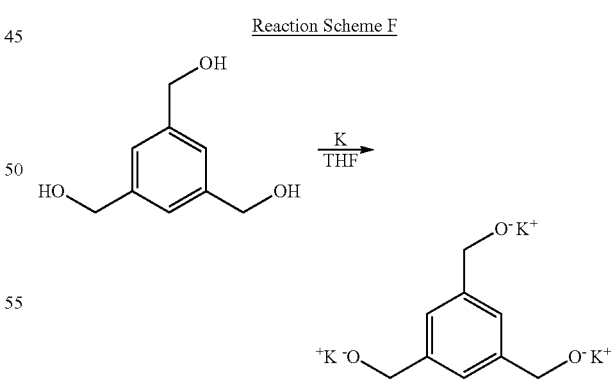

In general, functional groups may be introduced at the chain-ends of the carbohydrate polyethers of the present invention by the use of specific initiation or termination agents, while functionality along the polymer chain may be introduced or modified by post-polymerization reactions. This ability to introduce selective functionality into the polymers allows for the preparation of carbohydrate polyethers useful in the preparation of protein, peptide and drug conjugates. Polymers with non-reactive moieties such as alkyl at one terminus of the polymer chain are particularly useful for the homogeneous preparation of conjugates in the absence of cross-linking reactions. In certain embodiments, polymers of the present invention can be prepared with distinct reactive functional groups at the chain ends, wherein such heterobifunctional polymers are useful for applications such as targeted drug delivery and biosensors.

Examples of functional initiators for the anionic ring-opening polymerizations herein described included, but are not limited to, potassium 3,3-diethoxypropanolate, potassium 2-buthoxy ethanolate, dipotassium 3-thiolate-1-propionate and potassium allyl alkoxide. Allyl alkoxide is a particularly useful initiator since the resulting allyl ether end-group is easily converted a variety of other functionalities.

Examples of functional termination agents for the anionic ring-opening polymerizations herein described include, but are not limited to, alkyl halides, acylhalides, acid anhydrides, aldehydes, ethylene sulfide, ethylene oxide, 1,3-dibromoethane and 3-bromomethylpropyonate.

In other embodiments, chain initiation may be effected with a surface-bound initiator such as an alkali metal thiolate. Such a heterogeneous surface-bound initiator is useful for forming densely packed, brush type polymers, covalently bound to a surface such as silica. Surface initiation has the further advantage of low steric hindrance to attachment, since only a single monomer unit is attached at a time.

The 1,6:2,3-dianhydrohexopyranoses (Cerny epoxides) suitable as monomers for production of polymers of the present invention were prepared according to known methods starting from 1,6-anhydro-β-D-glucopyranose of general formula (X) also commonly known as levoglucosan. In a typical procedure, the levoglucosan hydroxyl moieties at C-2 and C-4 were converted to p-toluenesulfonate esters by treatment with p-toluenesulfonyl chloride in pyridine TsCl/Py). Subsequent treatment of the reaction mixture with a strong base, such as sodium methoxide in methanol (MeONa/MeOH), effected the regioselective formation of the 3,4-epoxide resulting in formation of 1,6:3,4-dianhydro-2-O-p-toluene-sulfonyl-β-D-galactopyranose (XII) (also referred to as TDG) without recovery of the di-p-toluenesulfonate intermediate (XI).

The TDG thus produced was conveniently purified via conventional crystallization processes. The overall synthetic scheme is illustrated below in Reaction Scheme G.

Reaction Scheme G

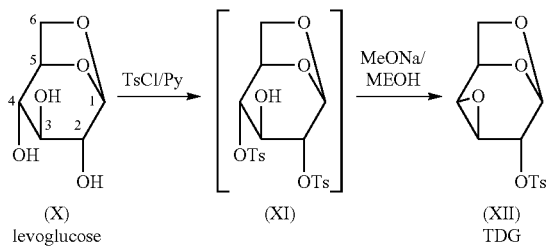

(X) levoglucose (XI) (XII) TDG

In a subsequent reaction a dianhydromannopyranose (XIV), also referred to herein as a DM monomer, was produced via the acid-catalyzed alcoholysis of 1,6:3,4-dianhydro-2-O-p-toluenesulfonyl-β-D-galactopyranose (XII) via treatment with an alcohol (ROH) in the presence of a suitable acid catalyst; wherein the 3,4-epoxy moiety was selectively cleaved to introduce the alcohol-derived R moiety at C-4 as depicted by formula (XIII). The subsequent treatment of the reaction mixture with a suitable base, such as sodium methoxide in methanol (MeONa/MeOH), effected the formation of a 2,3-epoxy moiety with concurrent with loss of the tosylate at C-2 to afford a dianhydromannopyranose (XIV). The overall process is illustrated below in Reaction Scheme H.

Reaction Scheme H

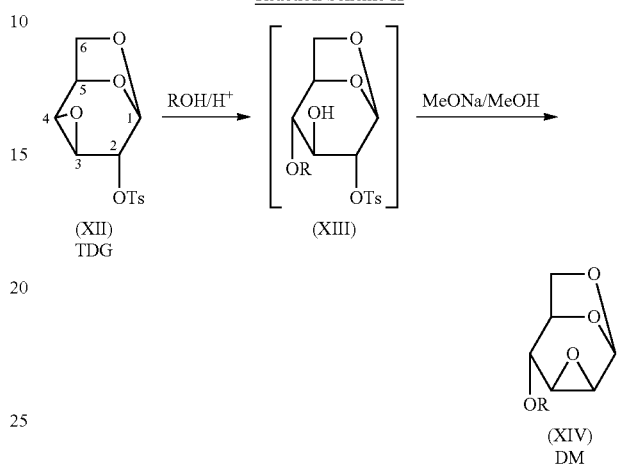

In certain preferred embodiments, C2-C3 linked carbohydrate polyethers compositions and derivatives thereof the present invention are covalently coupled or crosslinked to from a self-supporting macroreticular network. The required covalent coupling or crosslinking can be effected by any known method. For example, free-radical crosslinking can be effected by suitable chemical processes, suitable irradiation processes or combinations thereof. Suitable chemical free-radical initiators include azobisisobutyronitrile (AIBN), benzoyl peroxide and the like. Suitable high-energy irradiation sources include electron beam, ultra-violet (UV) and gamma irradiation. Additionally, crosslinking promoters such as bifunctional, trifunctional or tetrafunctional acrylates or methacrylate monomers and oligomers may be added to increase crosslinking efficiency and crosslink density. In other embodiments, self-supporting macroreticular networks are be produced by the covalent coupling or crosslinking blends of carbohydrate polyethers of the present invention with suitable active oligomers or polymers.

The water soluble RTG polymers of poly(2-3)-1,6-anhydro-β-D-glucopyranose (II) are often referred in text as DM polymers. Applications of reverse thermal gelation (RTG) polymers (DM polymers) of present invention include compositions for the treatment of constipation, encapsulation of sensitive mammalian cells, specifically for cell immobilization or encapsulation. Example of useful polymers for such applications include pMDM/DGDM copolymers, MW~33 k (30 mol % DGDM) wherein a solution (100 mg/L H$_2$O) remained a free flowing liquid at RT for at least 1 hr, whereupon heating the solution to ~30-40° C. resulted in a non-flowing gel that remained non-flowing and transparent for at least 4 hrs at 26° C. After 8 hrs, at 19° C. gel reverted to a viscous liquid, and wherein heating the solution to ~60° C. effected precipitation of the polymer.

Polymers of the present invention that exhibit reversible gel/liquid transitions are useful as drug delivery device system components, for example to formulate injectable drugs preferred polymers are liquid at or about RT, gels at body temp or above and capable of remaining gels in at body temp or below. Slow drug release is enabled by such gel formation. Rapid drug release is possible by heating injection site to effect release of drug by separating polymer, as a gel, from drug solution.

Polymer compositions of the present invention that exhibit reversible gel/liquid transitions are useful as injectable for sub-dermal maxiofacial applications such as wrinkle fill, lip augmentation, reduction of folds, removal of scars and the like similar to the manner in which hyaluronic acid and collagen are used in cosmetics procedures.

Polymer compositions of the present invention that exhibit reversible gel/liquid transitions are useful to augment of the body tissue in surgical procedures such as organ restoration, breast volume enhancement, eye surgery, knee restoration, ulcer treatment and the like. As well as use in eye surgery, e.g. corneal transplantation, cataract surgery, glaucoma surgery and surgery to repair retinal detachment. Such polymers are also useful as physiologic lubricants and as non-inflammatory vitreous substitutes to prevent scrapping of the endothelial cells as well as injectable agents for the treatment of arthritis particularly osteoarthritis of the knee.

Polymer compositions of the present invention that exhibit reversible gel/liquid transitions are useful in the synthesis of biological scaffolds for wound healing applications. Such scaffolds typically utilize proteins such as fibronectin attached to the hyaluronan to facilitate cell migration into the wound treatment for ankle and shoulder osteoarthritis pain. The DM polymers of the present invention are useful as tissue engineering products such as scaffolding and the like. Certain polymers of the present invention that exhibit reversible gel/liquid transitions are useful in combination with sodium bicarbonate or other agents to treat acid reflux and diarrhea Polymers of the present invention that exhibit reversible gel/liquid transitions are also useful encapsulation of mammalian cells such as islets by utilization of various spray techniques such as spraying a cold solution into a warm water vapor chamber.

Certain preferred RTG polymers of the present invention are random copolymers, terpolymers and the like or block polymers of MDM wherein p=0. The MDM homopolymers are not soluble in water and this component is used to modify LCST and $T_{gel}$ temperature of MEDM, DGDM and 3GDM polymers resulting in a family of thermosensitive polymers with gel transition temperature of 17° C. to 57° C.

Certain preferred RTG polymers of the present invention are copolymers of alkyl-DM (p=0, and the 4-O substituent is methyl, ethyl, propyl, and up to decyl) with MEDM, DGDM, 3GDM or 4GDM resulting in a family of thermosensitive polymers with Gel transition temperature of 5° C. to 100° C.

Certain other preferred RTG polymers of the present invention block copolymers of MDM or alkyl-DM with MEDM, DGDM and 3GDM having hydrophobic ("A") block segments and hydrophilic ("B") block segments. Such block copolymers are triblock copolymers (e.g., ABA or BAB) that exhibit reverse thermal gelation properties and are biodegradable as well as biocompatible. Importantly, such triblock copolymers of the present invention provide instant gelation and possess the necessary rate of degradation to be commercially useful. Certain other preferred RTG polymers comprising biodegradable hydrophobic A block segments include p-MDM, p-ethyl-DM, p-propyl-DM and higher analogs.

The preferred range of molecular weights for certain preferred polymers useful in the present invention can be readily determined by a person skilled in the art based upon such factors as the desired polymer degradation rate, viscosity, polymer concentration in the solution. Typically, the preferred range of molecular weight will be 1000 to 150,000 Daltons, although there is no actual limitation.

Certain TRG copolymer compositions of the present invention are specially regulated to assure retention of the desired water-solubility and gelling properties, i.e., monomer ratios must be such that the copolymers possess water solubility at temperatures below the LCST, and such that there is instant gelation under physiological conditions (i.e. pH 7.0 and 37° C.) so as to minimize the initial burst of drug. In certain hydrogels of the present invention the molar ratio of hydrophobic monomer is 0% to 90% and the hydrophilic B block is 10% to 100% of the copolymer.

The concentration at which certain useful block copolymers of the present invention remain soluble below the LCST and gel/precipitate above are generally up to about 60% by weight, with 1% to 30% preferred. The concentration utilized will depend upon the copolymer composition actually used, as well as whether or not a gel or suspension is desired.

The thermosensitive polymers of the present invention comprise derivatives of C2→C3 linked carbohydrate polyethers produced from monomeric 1,6:2,3-dianhydrohexopyranoses of formula (I). Such 1,6:2,3-dianhydrohexopyranoses of formula (I), which are also known variously as 1,6:2,3-dianhydro-4-O—R-β-D-mannopyranoses; 1,6:2,3-dianhydro-β-D-glucopyranoses and Cerny epoxides, have been utilized as intermediates in organic synthesis since the 1970s. The anionic ring-opening polymerization, under conditions for living polymerization, of 1,6:2,3-dianhydrohexopyranose of formula (I) where R=benzyl, methyl, allyl or hexadecyl has been reported by Berman et al., Polymer Science USSR 30: 481-487 (1988); Berman et al., Polymer Science U.S.S.R., vol. 30, no. 2, pp. 394-400 (1988) and Berman et al., Bioorganischeskaya Khimiya, vol. 11, no. 8, pp. 1125-1129, 1985. These polymers were not soluble in water.

The process used to mix the TRG polymers with a biologically active agent and/or other materials involves dissolving the polymers in an aqueous solution, followed by addition of the biologically active agent (in solution, suspension or powder), followed by thorough mixing to assure a homogeneous mixing of the biologically active agent throughout the polymer. Alternatively, the process can involve the dissolving of the TRG polymer in a biologically active agent-containing solution. In either case, the process is conducted at a temperature lower than the gelation temperature of the copolymer and the material is implanted into the body as a solution, which then gels or solidifies into a depot in the body. The biologically active agent will generally have a concentration in the range of 0 to 200 mg/mL.

Useful buffers in the preparation of the biologically active agent-containing hydrogels of the present invention are buffers which are all well known by those buffers known in the art and include, but are not limited to, sodium acetate, Tris, sodium phosphate, MOPS, PIPES, MES and potassium phosphate, in the range of 25 mM to 500 mM and in the pH range of 4.0 to 8.5.

It is also envisioned that other excipients, e.g., various sugars, salts, or surfactants, may be included in the biologically active agent-containing hydrogels of the present invention in order to alter the LCST or rate of gelation of the gels. The ability to alter the rate of gelation and/or LCST is important and an otherwise non-useful hydrogel may be made useful by addition of such excipients. For examples 0.9% of NaCl is lowers Temperature of gelation 1-2° C. compared to pure water. Examples of such additives include sodium chloride or zinc chloride in the range of 0.5% to 10%, glucose or sucrose in the range of 5% to 20%

As used herein, biologically active agents refers to small organic molecules, stem cells, inactivated viruses or cells intended for vaccinations, recombinant or naturally occurring proteins, whether human or animal, DNA or RNA molecules, useful for prophylactic, therapeutic or diagnostic or vaccination application. The biologically active agent can be natural, synthetic, semi-synthetic or derivatives thereof. In addition, biologically active agents of the present invention can be perceptible. A wide range of biologically active agents are useful in certain embodiments of the present invention. Such agents include, but are not limited to, hormones, cytokines, hematopoietic factors, growth factors, anti-obesity factors, trophic factors, anti-inflammatory factors, small molecules, nucleic acids, polypeptides and enzymes. One skilled in the art will readily be able to adapt a desired biologically active agent to the compositions of present invention.

Proteins contemplated for use would include but are not limited to interferon consensus (see, U.S. Pat. Nos. 5,372,808, 5,541,293 4,897,471, and 4,695,623 hereby incorporated by reference including drawings), interleukins (see, U.S. Pat. No. 5,075,222, erythropoietins (see, U.S. Pat. Nos. 4,703,008, 5,441,868, 5,618,698 5,547,933, and 5,621,080), granulocyte-colony stimulating factors (see, U.S. Pat. Nos. 4,810,643, 4,999,291, 5,581,476, 5,582,823, and PCT Publication No. 94/17185), stem cell factor (PCT Publication Nos. 91/05795, 92/17505 and 95/17206), and leptin (OB protein) (see PCT publication Nos. 96/40912, 96/05309, 97/00128, 97/01010 and 97/06816).

Also included are those polypeptides with amino acid substitutions, which are "conservative" according to acidity, charge, hydrophobicity, polarity, size or any other characteristic known to those skilled in the art. Polypeptides or analogs thereof may also contain one or more amino acid analogs, such as peptidomimetics.

In general, comprehended by the invention are pharmaceutical compositions comprising effective amounts of biologically active agents, together with pharmaceutically acceptable diluents, preservatives, solubilizers, emulsifiers, adjuvants and/or carriers needed for administration. The optimal pharmaceutical formulation for a desired biologically active agent will be determined by one skilled in the art depending upon the route of administration and desired dosage. Exemplary pharmaceutical compositions are disclosed in Remington's Pharmaceutical Sciences (Mack Publishing Co., 18th Ed., Easton, Pa., pgs. 1435-1712 (1990)).

The pharmaceutical compositions of the present invention are administered as a liquid via intramuscular or subcutaneous route and undergo a phase change wherein a gel is formed within the body, since the body temperature will be above the gelation temperature of the material. The release rates and duration for the particular biologically active agents will be a function of, inter alia, hydrogel density and the molecular weight of the agent.

Therapeutic uses of the compositions of the present invention depend on the biologically active agent used. One skilled in the art will readily be able to adapt a desired biologically active agent to the present invention for its intended therapeutic uses.

In addition, the present polymers and compositions may also be used for manufacture of one or more medicaments for treatment or amelioration of the conditions the biologically active agent is intended to treat.

In the sustained-release compositions of the present invention, an effective amount of active ingredient will be utilized. As used herein, sustained release refers to the gradual release of active ingredient from the polymer matrix, over an extended period of time. The sustained release can be continuous or discontinuous, linear or non-linear, and this can be accomplished using one or more polymer compositions, drug loadings, selection of excipients, or other modifications. The sustained release will result in biologically effective serum levels of the active agent (typically above endogenous levels) for a period of time longer than that observed with direct administration of the active agent. Typically, a sustained release of the active agent will be for a period of a week or more, preferably up to one month and in some applications up to 12 months.

In certain compositions the bioactive agent is a small molecule drug including, but not limited to, acne reducing drugs, antibiotics, antivirals, antifungals, antineoplastics, antiangiogenics, antiarrhythmics, antiparkinson drugs, anticoagulants, anticonvulsants, anticancer drugs, antiallergic drugs, antidepressants, antidiabetic drugs, antihistamines, antihypertensives, antimigraine drugs, antipsychotics, anxiolytics, sedatives, hypnotics, bile acid sequestrants, bisphosphonates, bone resorption inhibitors, bronchodilators, lipid-lowering drugs, cardiovascular drugs, central nervous system drugs, chelating agents, cholesterol absorption inhibitors, contraceptives, decongestants, dermatological agents, diagnostic agents, radiopharmaceuticals, diuretics, expectorants, drugs used in treating alcohol, tobacco and illegal drug dependence, fibric acid drugs, gastrointestinal drugs, general anesthetics, growth hormones, heparins, heparin antagonists, herbal products, immunologic agents, immunosuppressants, insulin, inotropic agents, interferons, mast cell stabilizers, mouth, nose and throat drugs, muscle relaxants, nutritional products, ophthalmic drugs, antibiotic drugs, probiotics, psychotherapeutic drugs, radiological agents, respiratory drugs, sex hormones, spermicidal agents, statins, thrombolytics, thyroid drugs, vaginal preparations, vitamins and the like.

In certain other compositions a list of useful bioactive agents includes, but is not limited to, hormones, receptors, cytokines, hematopoietic factors, growth factors, anti-obesity factors, trophic factors, anti-inflammatory factors, small molecule drugs, nucleic acids, proteins, polypeptides, antibodies, enzymes and the like.

Certain polymers useful in embodiments of the present invention are carbohydrate polyethers, which can be linear or non-linear and can be homopolymers, copolymers or combinations thereof. The non-linear polymers of the invention can have a variety of architectures, including for example star-polymers, branched polymers, graft polymers, cross-linked polymers, semi-cross-linked polymers and the like or combinations thereof. These various polymer architectures are achieved with a high degree of control by the polymer preparation methods of the invention.

The following examples are presented as illustrations of embodiments of the present invention and should not be construed to limit the scope of the invention in any way.

Example 1

Synthesis of 1,6:3,4-dianhydro-2-O-p-toluenesulfo-nyl-β-D-galactopyranose (TDG) as starting material for D-mannopyranose monomer syntheses To a solution of 162 g of levoglucosan in 500 mL of anhydrous pyridine and 500 mL of anhydrous acetone was added 400 g of p-toluenesulfonylchloride in small portions. The resulting reaction mixture was stirred at ambient temperature for 72 hrs. after which time 1.0 L of chloroform and 1.0 L of water were added. The aqueous layer was separated and extracted with chloroform (2×200 mL). The combined chloroform extract was washed sequentially with water (3×1000 mL), 10% $H_2SO_4$ at pH 4 (2×850 mL), concentrated $Na_2CO_3$ (300 mL), water (3×500 mL) and reduced in vacuo to syrup. The syrup was dissolved in 1000 mL of anhydrous chloroform and 200 mL of anhydrous methanol and to this solution was added a solution of sodium methoxide (prepared from 69 g of sodium in anhydrous methanol) at ambient temperature in small portions and the resulting reaction mixture was stirred for 12 hrs. at ambient temperature. To this mixture was added 1000 mL of water and the aqueous layer was extracted with chloroform (2×200 mL). The combined chloroform extract was washed with water (3×800 mL), reduced in vacuo, crystallized and then recrystallized from methanol. Yield=178 g (60%) of white needles; MP=150° C.; $[\alpha]_D=-37°$ ($CHCl_3$); single spot by thin layer chromatography (TLC).

Example 2

Synthesis of 1,6:2,3-dianhydro-4-O-benzyl-β-D-mannopyranose (BDM)

To a solution of 28 g of TDG in 100 mL of benzene and 72 mL of benzyl alcohol in a flask equipped with a Dean-Stark water separator was added 3 g of p-toluenesulfonic acid monohydrate. The reaction mixture was heated to reflux for 5 hrs., while the progress of the reaction was monitored by TLC ($CHCl_3$/acetone, 9/1, v/v). After the ring-opening reaction was complete 100 mL of chloroform was added followed by addition of the solution of 6.9 g of sodium in 100 mL of anhydrous methanol and the progress of the reaction was monitored by TLC. After the ring-closing reaction was complete, chloroform (50 mL) and water (200 mL) were added and the organic layer was separated, extracted with water and reduced in vacuo to syrup. The syrup was distilled under high vacuum and crystallized from diethyl ether and recrystallized from anhydrous ether. Yield=14.43 g (62%); colorless crystals MP=60° C.; single spot on TLC; $[\alpha]_D=-28°$ ($CHCl_3$).

Example 3

Synthesis of 1,6:2,3-dianhydro-4-O-decyl-β-D-mannopyranose (DDM)

To a solution of 30 g of TDG in 60 mL of benzene and 90 mL of 1-decanol in a flask equipped with a Dean-Stark water separator was added 3.1 g of p-toluenesulfonic acid monohydrate. The reaction mixture was heated to reflux for 5 hrs., while the progress of the reaction was monitored by TLC ($CHCl_3$/acetone, 9/1, v/v). After the ring-opening reaction was complete 100 mL of chloroform and 28 mL of methanol was added followed by addition of the solution of 3.5 g of sodium in 56 mL of anhydrous methanol and the progress of the reaction was monitored by TLC. After the ring-closing reaction was complete, chloroform (100 mL) and water (100 mL) was added and the organic layer was separated, extracted with water, and reduced in vacuo to syrup. Fractional distillation of syrup in high vacuum yielded 23.4 g (83%) of colorless viscous liquid, pure by HPLC., single spot on TLC; $[\alpha]D=-24.8°$ ($CHCl_3$). Structure identification: $^{13}C/^1H$ HMQC NMR spectra. This (DDM) monomer and the polymer synthesized there from were soluble in hexane.

Example 4

Synthesis of 1,6:2,3-dianhydro-4-O-(2-methoxyethyl)-β-D-mannopyranose (MEDM)

To a solution of 30 g of TDG in 60 mL of benzene and 32 mL of 2-methoxyethanol in a flask equipped with a Dean-Stark water separator was added 3.1 g of p-toluenesulfonic acid monohydrate. The reaction mixture was heated to reflux for 6 hrs. while the progress of the reaction was monitored by TLC ($CHCl_3$/acetone, 9/1, v/v). After the ring-opening reaction was complete 100 mL of chloroform and 28 mL of methanol was added followed by addition of the solution of 3.5 g of sodium in 56 mL of anhydrous methanol and the progress of the reaction was monitored by TLC. After the ring-closing reaction was complete, chloroform (100 mL) and water (100 mL) was added and the organic layer was separated, water layer extracted with chloroform, combined and reduced in vacuo to syrup. Fractional distillation of syrup in high vacuum yielded 14.5 g (71%) of colorless viscous liquid, pure by HPLC, single spot on TLC; $[\alpha]D=-34.6°$ ($CHCl_3$). Structure identification: $^{13}C/^1H$ HMQC NMR spectra. This (MEDM) monomer and the polymer synthesized there from were soluble in water.

Example 5

Synthesis of 1,6:2,3-dianhydro-4-O-neopentyl-β-D-mannopyranose (NPDM)

To a solution of 30 g of TDG in 60 mL of benzene and 50 g of 2,2-dimethyl-1-propanol in a flask equipped with a Dean-Stark water separator was added 3.1 g of p-toluenesulfonic acid monohydrate. The reaction mixture was heated to reflux for 6 hrs. while the progress of the reaction was monitored by TLC ($CHCl_3$/acetone, 9/1, v/v). After the ring-opening reaction was complete 100 mL of chloroform and 28 mL of methanol was added followed by addition to the solution of 3.5 g of sodium in 56 mL of anhydrous methanol and the progress of the reaction was monitored by TLC. After the ring-closing reaction was complete, chloroform (100 mL) and water (100 mL) was added and the organic layer, the organic layer was separated, extracted with water, and reduced in vacuo to syrup. Distillation of the syrup in vacuum yielded 16.8 g (78%) of white solid. The recrystallization from ether/hexane yielded 10.3 g of colorless crystals, single spot on TLC; $[\alpha]D=-37.5°$ ($CHCl_3$). Structure identification: $^{13}C/^1H$ HMQC NMR spectra. The polymers of this (NPDM) monomer are insoluble in all common solvents and precipitate during polymerization.

Example 6

Purification of Solvents

Polymerization grade tetrahydrofuran (THF) was prepared by refluxing dry THF over sodium/benzophenone until the solution develops a deep blue color. The THF was then distilled and stored in the dry box or over potassium/sodium alloy in a dry box. Potassium/sodium alloy can be prepared in a dry box by melting K and Na (70/30 w/w) and then separating pure liquid alloy from oxides by passing it through a capillary tube.

Example 7

Preparation of Anionic Polymerization Initiators

Monofunctional and trifunctional anionic initiators were prepared by the reactions of 2-butoxyethanol or 1,3,5-benzenetrimethanol in THF solution with an excess of potassium metal. The initiators thus prepared were stored over potassium metal in a dry box or in a dry box alone. The concentration of initiator in solution could be determined by reverse titration.

Example 8

Polymerization of the DM monomers

The DM monomers as prepared by the methods exemplified in Examples 1-5 above were converted to polymers by the anionic polymerization reaction as illustrated in Reaction Scheme A and the physical properties of homopolymers of differing monomers are presented in Table 1. With reference to Table 1 it should be noted that all of the resulting polymers have very low poly dispersity (Mw/Mn). The polymers wherein R=2-methoxyethyl and R=ethoxy-2-methoxyethyl are water-soluble while the polymers wherein R=neopentyl and R=isopropyl are insoluble in all common solvents and the polymers wherein R=n-octyl and R=n-decyl are soluble in hexane. Water-soluble polymers are particularly useful in biological applications such as surface protection from non-specific adsorption. The data also illustrates that the glass transition temperature (Tg) of polymers with alkyl substituents decreases as the alkyl chain length increases. Solutions of DM polymers wherein R=isobutyl in solvents, such as chloroform and THF exhibit non-newtonian behavior (shear dependent viscosity). The DM polymers wherein R=2-methoxyethyl and R=ethoxy-2-methoxyethyl show lower critical solution temperature (LCST) behavior.

TABLE 1

| R | Monomer $[\alpha]_D$ (deg) | Polymer $[\alpha]_D$ (deg) | Polymer Tg/Tm (° C.) | Polymer Solubility[4] | Polymer Mn | Polymer Mw/Mn | DP |
|---|---|---|---|---|---|---|---|
| 1 methyl | −44.70 | −73.0 | 163.6 | R | 65,835 | 1.130 | 417 |
| 2 allyl | −35.90 | −59.6 | n/m | R | 48,896 | 1.107 | 266 |
| 3 n-pentyl | −33.35 | −72.3 | 84.1 | R | 94,497 | 1.040 | 442 |
| 4 n-hexyl | −30.46 | −71.6 | 65.0 | R | 60,314 | 1.030 | 265 |
| 5 n-octyl | −28.34 | −67.5 | 35.2 | R, H | 55,786 | 1.030 | 218 |
| 6 n-decyl | −24.82 | −59.2 | 13.5 | R, H | 43,783 | 1.046 | 154 |
| 7 2-methoxyethyl | −34.58 | −50.4 | 89.9 | R, W, M | 74,057 | 1.07 | 366 |
| 8 ethoxy-2-methoxyethyl | −26.36 | −41.0 | 17.5 | R, W, M | 24,667 | 1.030 | 100 |
| 9 isoamyl | −34.49 | −75.5 | 115.9 | R | 100,539 | 1.070 | 469 |
| 10 isobutyl | −35.20 | −67.0 | 157.1 | Temp Dep.[B] | 145,050 | 1.13 | 725 |
| 11 benzyl | −28.30 | −41.0 | 106.6 | R | 120,788 | 1.06 | 516 |
| 12 neopentyl | −37.50 | n/m | 160.4 | insoluble | n/m | n/m | n/m |
| 13 isopropyl | −36.72 | n/m | n/m | insoluble | n/m | n/m | n/m |

[A]R = tetrahydrofuran, chloroform, methylene chloride, pyridine and similar polar organic solvents; H = heptane or other non-polar organic solvents; W = water; and M = methanol or other alcohols.

Example 9

Polymers of 1,6:2,3-dianhydro-4-O-(2-methoxyethyl)-β-D-mannopyranose (MEDM)

A series of water-soluble polymers of the MEDM monomer of example 4 was prepared by the synthesis route illustrated in Reaction Scheme A by initiation with potassium 3,3-diethoxypropanolate, wherein the ratio of monomer/initiator was varied from 9 to 643. Results are presented in Table 2, wherein these data clearly show that the molecular weight (Mn) was conveniently controlled by the initial ration of monomer/initiator while the poly dispersity index (Mw/Mn) remained substantially constant.

TABLE 2

| Run No. | Monomer/Init. | Mn | Mw/Mn (PDI) | Deg. Polyn. |
|---|---|---|---|---|
| 1 | 9 | 2,735 | 1.195 | 14 |
| 2 | 10 | 2,860 | 1.112 | 14 |
| 3 | 19 | 4,456 | 1.089 | 22 |
| 4 | 20 | 5,351 | 1.133 | 26 |
| 5 | 43 | 8,188 | 1.070 | 41 |
| 6 | 67 | 12,257 | 1.055 | 61 |
| 7 | 120 | 18,106 | 1.041 | 90 |
| 8 | 216 | 29,264 | 1.037 | 145 |
| 9 | 358 | 48,266 | 1.044 | 239 |
| 10 | 643 | 74,057 | 1.071 | 366 |

Example 10

1,6:2,3-dianhydro-4-O-pentyl-β-D-mannopyranose (PDM)

A series of polymers of the PDM monomer was prepared by the synthesis route illustrated in Reaction Scheme A by initiation with potassium 3,3-diethoxypropanolate, wherein the ratio of monomer/initiator was varied from 20 to 948. Results are presented in Table 3, wherein these data clearly show that the molecular weight (Mn) was conveniently controlled by the initial ration of monomer/initiator while the poly dispersity index (Mw/Mn) remained substantially constant.

TABLE 3

| Run No. | Monomer/Init. | Mn | Mw | Mw/Mn (PDI) | Deg. Polyn. |
|---|---|---|---|---|---|
| 1 | 20 | 8531 | 9210 | 1.080 | 40 |
| 2 | 40 | 13857 | 14599 | 1.054 | 65 |
| 3 | 99 | 20752 | 21630 | 1.042 | 97 |
| 4 | 198 | 31868 | 33174 | 1.041 | 149 |
| 5 | 512 | 63422 | 65606 | 1.034 | 296 |
| 6 | 948 | 85840 | 89028 | 1.037 | 401 |

Example 11

Synthesis of poly(2-3)-1,6-anhydro-4-O-benzyl-b-D-glucopyranose (pBDM)

Figure 2:
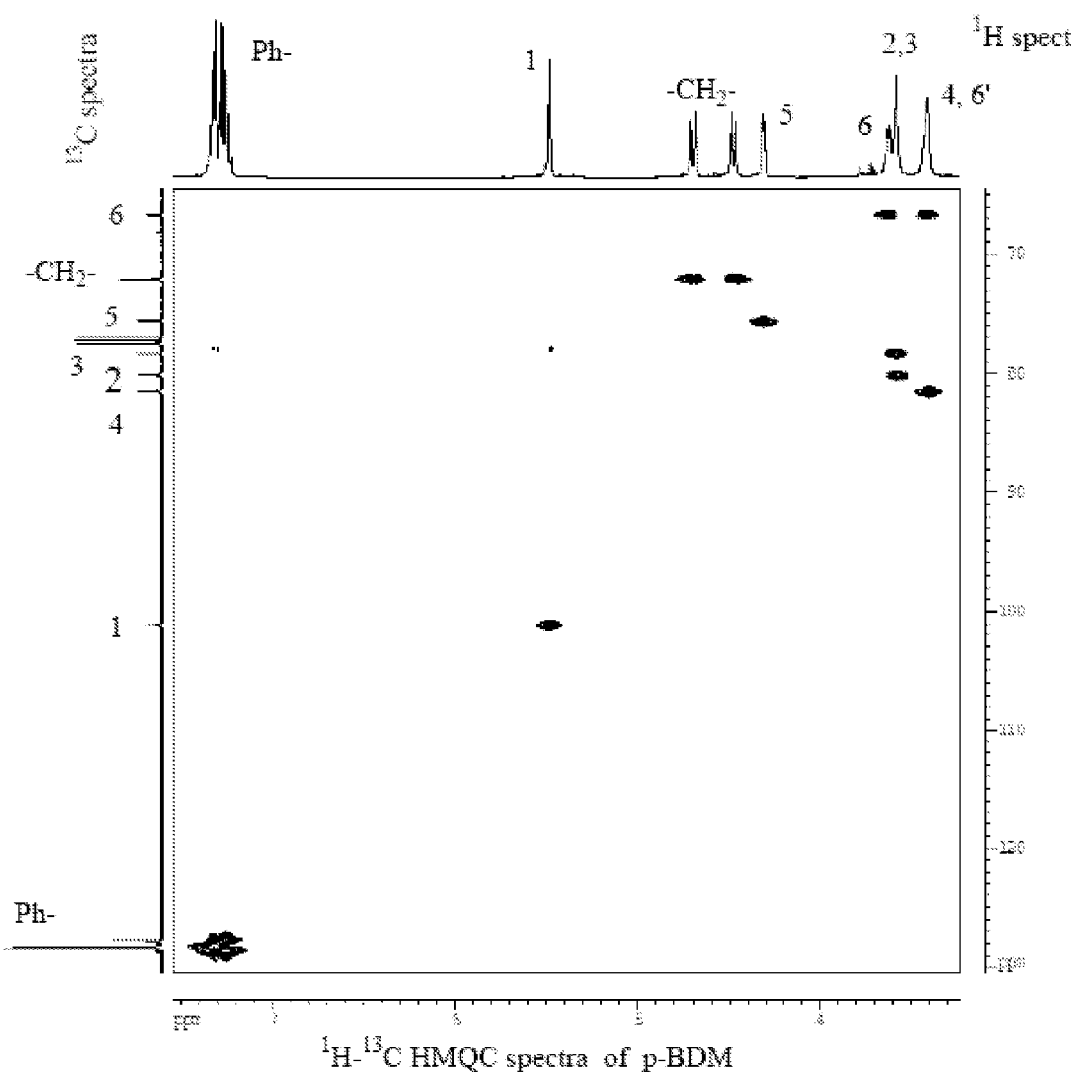
FIG. 2 presents the $^1H$—$^{13}C$ HMQC spectrum of poly(2-3)-1,6-anhydro-4-O-benzyl-β-D-glucopyranose.

All steps were performed in an argon-filled dry box. In a sealable vial, 1.00 g of BDM monomer was dissolved in 1.0 g of THF followed by addition of 0.058 g of a solution of potassium 3,3-diethoxypropanolate in THF. The vial was capped, sealed (crimped) and the reaction mixture was incubated at 60° C. for 12 hrs. The reaction mixture was then diluted with 2 mL of CHCl3 and the polymer was precipitated into 50 mL of methanol. No residual monomer was found by TLC and GPC in the polymerization mix. Polymer was isolated by centrifugation and then dried in vacuum at ambient temperature. Yield: 1.0 g (100%); Mn=49798, Mw=89,410. The stereospecificity and regiospecificity of the polymer was determined to be 100% by $^{13}$C and $^{1}$H NMR spectroscopy. Full peak assignment in NMR spectra was accomplished via $^{1}$H—$^{1}$H COSY and $^{1}$H—$^{13}$C HMQC techniques. All NMR spectra were obtained on Bruker Cryo500 instrument. Polymer structure was confirmed by $^{13}$C and $^{1}$H nmr peak assignments. The $^{1}$H—$^{13}$C HMQC spectra are presented in FIG. 2.

Example 12

Synthesis of poly(2-3)-1,6-anhydro-D-glucopyranose (pDM)

In a flask, 1.0 g of pBDM polymer from example 11 was dissolved in 18 g of THF and added in small portions to the solution of 89 mg of lithium metal in 65 g of THF containing 2.2 g of naphthalene at −25 to −26° C. over 13 min. The reaction mixture was stirred at −28 to −18° C. for 95 min, 6.5 mL of 14% NH$_4$Cl solution was added, white precipitate was washed with THF and water and dried in vacuo. Yield=0.595 g (97% theory). This polymer is insoluble in water, THF and CHCl$_3$, and is soluble in DMF.

Example 13

Poly(2-3)-1,6-anhydro-4-O-(3,5-dimethylphenylcarbamate)-β-D-glucopyranose (DMPC)

In a flask 0.593 g of pDM polymer from example 4b was stirred with 2.09 mL of 3,5-dimethylphenyl isocyanate and 10.5 mL of dry pyridine at 80° C. for 24 hrs. The solution was cooled to ambient temperature and polymer precipitated into 50 mL of methanol, collected, dissolved in 5 mL of chloroform and re-precipitated in methanol, dried in vacuo at ambient temperature. Yield=1.05 g (97% theory).

Example 14

Preparation of (pDGDM-pODM-pDGDM) Triblock Polymers

An ABA triblock polymer (pDGDM-pODM-pDGDM) was synthesized from 0.4 g of DGDM monomer which was mixed with 0.5 g of THF and 0.105 g 100 mM solution of potassium 2-butoxyethanolate and incubated at 60° C. for 6 hrs., then 0.4 g of ODM monomer was added and mixture was incubated for an additional 6 hrs. at 60° C., then 0.4 g of DGDM monomer was added and reaction mixture was incubated at 60° C. for 6 hrs . Terpolymer was precipitated in 50 mL of ether. Yield=1.0 g, Mn=38,149, Mw=40,171. This block copolymer formed an opaque solution in water.

Example 15

Preparation of (pODM-pDGDM-pODM) Triblock Polymers

An ABA triblock polymer (pODM-pDGDM-pODM) was synthesized from 0.4 g of ODM monomer which was mixed with 0.5 g of THF and 0.105 g 100 mM solution of potassium 2-butoxyethanolate and incubated at 60° C. for 6 hrs., then 0.4 g of DGDM monomer was added and mixture was incubated for an additional 6 hrs. at 60° C. followed by addition of 0.4 g of ODM monomer was added, incubated at 60° C. for 6 hrs. Resulting terpolymer was precipitated in 50 mL of ether. Polymer formed an opaque solution in hexane. Yield 0.97 g, Mn=51.699, Mw=53.554.

Example 16

Poly(2-3)-1,6-bis(3,5-dimethylphenylcarbamate)-4-O-benzyl-β-D-glucopyranose (bis-DMPC)

To a solution of 0.56 g pBDM polymer in 2.87 mL of acetic anhydride was added 10 μL of concentrated sulfuric acid. The reaction mixture was incubated at ambient temperature for 1 hr and then poured into 100 mL of ice/water mix. Polymer precipitate was collected, washed with water and dried in vacuo. Yield=0.59 g (68%): poly(2-3)-1,6-di-O-acetyl-4-O-benzyl-D-glucopyranose. This polymer was dissolved in 2.5 mL of THF, a solution of 0.14 g of sodium in 2.0 ml of methanol was added and reaction mixture was incubated at ambient temperature for 1 hr, the polymer precipitate was collected and washed with methanol and ether. Yield=0.27 g (65%): poly(2-3)-4-O-benzyl-D-glucopyranose. A 0.27 g portion of this polymer was stirred with 0.49 mL of 3,5-dimethylphenyl isocyanate and 5.4 mL of dry pyridine at 80° C. for 24 hrs. The solution was cooled to ambient temperature and polymer precipitated in 50 mL of methanol. The precipitate was dissolved in 5 mL of chloroform and re-precipitated in methanol and dried in vacuo at ambient temperature. Yield=0.6 g (90%) poly(2-3)-1,6-bis(3,5-dimethylphenylcarbamate)-4-O-benzyl-D-glucopyranose (bis-DMPC).

Example 17

Synthesis of TRG Polymers

Synthesis of random copolymer of MDM and DGDM (60/70 mol %) (pM/DGDM-8, with Tgel=30° C. is used here as an example. Reaction mixture containing MDM, 0.422 g; DGDM 0.310 g, THF, 0.7 g and 0.164 g of 57 mM solution of potassium 2-butoxyethoxylate in THF was crimped in a vial and incubated at 60° C. for 12 hrs. All polymerization experiments are performed in an argon-filled glove box. The polymerization mix was diluted with 2 mL of THF and polymer precipitated into 50 mL of ether, centrifuged and dried in vacuum. Polymer recovery was 0.730 g (99.7%). No residual monomer was found by GPC in the polymerization mix. Mn=32,613, Mw=33,945, Mw/Mn=1.041. 100% Stereo and regio-specificity of the polymer is established by $^{13}$C and $^{1}$H NMR spectroscopy. Full peak assignments in NMR spectra is accomplished by running $^{1}$H—$^{1}$H COSY and $^{1}$H—$^{13}$C HMQC experiments. Polymer is soluble in cold water and will form non-flowing gel at and above 30° C. for concentrations 5 and 10% and above.

Example 18

Random Copolymer: pDGDM-pADM

In a sealed vial 0.5 g of DGDM (1,6:2,3-dianhydro-4-O-ethoxy-2-methoxyethyl-b-D mannopyranose), 0.03 g of ADM (1,6:2,3-dianhydro-4-O-allyl-b-D mannopyranose), 0.5 mL of THF and 0.193 g of 210 mmolar dipotassium 3-thiolate-1-propionate in THF are mixed and incubated at 60° C. for 48 hrs. The resulting polymer is precipitated into methanol collected and dried.

Example 19

Initiation with Potassium 2-Butoxy Ethanolate and Termination with Succinic Anhydride In a vial 0.5 g of ODM (1,6:2,3-dianhydro-4-O-octyl-β-D mannopyranose), 0.5 mL of THF and 0.175 g of 200 mmolar of potassium 2-butoxy ethanolate in THF were mixed and incubated at 60° C. for 12 hrs. The polymerization reaction was terminated by addition of 0.175 g of 400 mmolar succinic anhydride solution in THF. The resulting polymer was precipitated from methanol. Yield=0.36 g; Mn=27,402, Mw/Mn (PD)=1.048

Example 20

Introduction of Carboxylic End-Groups (a) To a sealable vial was added 0.5 g of 1,6:2,3-dianhydro-4-O-pentyl-β-D mannopyranose (PDM), 0.5 mL THF and 0.193 g of 210 mmolar dipotassium 3-thiolate-1-propionate in THF. Reactants were mixed, vial was sealed and reaction mixture was incubated at 60° C. for 48 hrs. The resulting polymer was precipitated into methanol. Yield=0.101 g; Mn=23,969; Mw/Mn (PD)=1.085

(b) To a sealable vial was added 0.5 g of 1,6:2,3-dianhydro-4-O-octyl-β-D mannopyranose (ODM), 0.5 mL of THF and 0.175 g of 200 mmolar of potassium 2-butoxy ethanolate in THF. Reactants were mixed, vial was sealed and reaction mixture was incubated at 60° C. for 12 hrs. The reaction was terminated by addition of 0.175 g of 400 mmolar succinic anhydride solution in THF. The resulting polymer was precipitated from methanol. Yield=0.36 g; Mn=27,402, Mw/Mn (PD)=1.048

Example 21

27.8 mg of a pMDM/DGDM copolymer, MW~33 k (30 mol % DGDM), was dissolved in 278 uL $H_2O$ at 5° C. The solution remained a free-flowing liquid at ambient temperature for at least 1 hr, whereupon heating the solution to ~30-40° C. converted the solution to a non-flowing gel. The gel remained non-flowing and transparent at ambient temperature for more than 4 hrs. and at 26° C. for 8 hrs. At 19° C. the gel became a slow flowing viscous liquid. Upon heating the solution to ~60° C. the gel separated and the polymer precipitated from the solution.

Example 22

Synthesis of 1,6:2,3-dianhydro-4-O-2-(2-Methoxyethoxy)ethoxy-β-D-mannopyranose (DGDM monomer)

41.7 g of TDG_(22) was dissolved in 83 mL of benzene and 82 mL of diethylene glycol methyl ether, 4.3 g of p-toluenesulfonic acid monohydrate was added and reaction was refluxed with Dean-Stark apparatus for 5 hrs. Reaction progress was monitored by TLC ($CHCl_3$/Acetone, 9/1, v/v). When ring-opening reaction was complete, 39 mL of methanol was added followed by addition of the solution of 4.83 g of sodium in 77 mL of anhydrous methanol. The progress of the reaction was monitored by TLC. When ring closure reaction was complete, chloroform (50 mL) and water (200 mL) were added, organic layer separated, water layer extracted with $CHCl_3$, combined, and solvent was removed in vacuo to afford a viscous liquid residue. The residue was dissolved in water, filtered, concentrated and distilled under high vacuum. Fractional vacuum distillation yielded 26 g of DGDM (75%), as a colorless liquid, single peak by HPLC and TLC. $[a]_D$=−26.4° ($CHCl_3$).

Example 23

Synthesis of a poly(2-3)-1,6-anhydro-4-O-methyl/co-2-(2-Methoxyethoxy)ethoxy-β-D-glucopyranose copolymer A reaction mixture containing, 0.422 g MDM; 0.310 g DGDM, 0.7 g THF, and 0.164 g of a 57 mM solution of potassium 2-butoxyethoxylate in THF was sealed in a vial and incubated at 60° C. for 12 hrs. in an argon-filled glove box. The polymerization mixture was then diluted with 2 mL of THF and polymer was precipitated into 50 mL of ether, centrifuged and dried in vacuo. Product recovery was 0.730 g (99.7%). No residual monomer was found in the polymerization mix by GPC. Mn=32,613, Mw=33,945, Mw/Mn=1.041. A 100% stereospecificity and regiospecificity of the polymer was established by $^{13}C$ and $^1H$ NMR spectroscopy. Full peak assignments in NMR spectra were accomplished by $^1H$—$^1H$ COSY and $^1H$—$^{13}C$ HMQC. Polymer product was soluble in cold water and formed a non-flowing gel at and above 30° C. at concentrations of 5% and 10% or greater. Other copolymers of MDM and DGDM may be readily synthesized by the same or similar procedures.

Example 24

Gelation Temperatures of Water-Soluble Carbohydrate Polyethers

Figure 3:
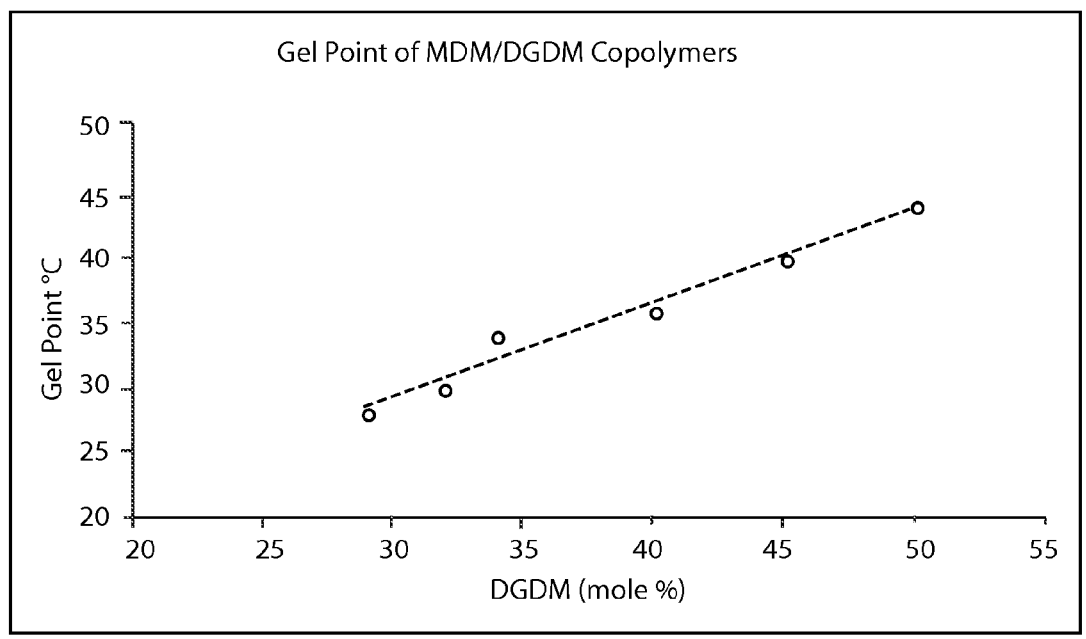
FIG. 3 presents a graph of Gel Temp. vs. Mol % DGDM in MDM/DGDM copolymers.

To determine gelation temperature, water-soluble polymers of the present invention were dissolved in water at 10% w/v and solution temperature was increases at approximately 2° C./min as the viscosity of the solution was monitored with rheometer (TA Instruments, model number AR-62). The lowest temperature at which the solution ceased to flow was recorded as the gelation temperature. Gelation temperatures of representative water-soluble carbohydrate polyethers of the present invention as determined by the procedure described herein are presented in Table 5 and a graph showing the gelation temperature (Gel Point) vs. Mol % DGDM in MDM/DGDM copolymers is presented in FIG. 3.

TABLE 5

| | Gel Temp (° C.) | MDM (mole %) | MEDM (mole %) | DGDM (mole %) | 3GDM (mole %) |
|---|---|---|---|---|---|
| pMDMDM/MEDM-58 | 17 | 50 | 50 | | |
| pMDMDM/MEDM-59 | 23 | 25 | 75 | | |
| pMDM/DGDM-53 | 28 | 71 | | 29 | |
| pMDM/DGDM-8 | 30 | 68 | | 32 | |
| pMDM/DGDM-62 | 34 | 66 | | 34 | |
| pMDM/DGDM-56 | 36 | 60 | | 40 | |
| pMDM/DGDM-63 | 40 | 55 | | 45 | |
| pMDM/DGDM-50 | 44 | 50 | | 50 | |
| pMDM/3GDM-67 | 38 | 78 | | | 22 |
| pMDM/3GDM-68 | 40 | 66 | | | 34 |
| pMDM/3GDM-69 | 44 | 49 | | | 51 |
| pMDM/ME/DGDM-65 | 27 | 50 | | 38 | |

TABLE 5-continued

|  | Gel Temp (° C.) | MDM (mole %) | MEDM (mole %) | DGDM (mole %) | 3GDM (mole %) |
|---|---|---|---|---|---|
| pMDM/ME/DGDM-66 | 29 | 59 | 20 |  |  |
| pMDM/ME/DGDM-64 | 34 | 49 | 25 |  |  |

Example 25

Gelation Temperatures of Water-Soluble Carbohydrate Polyethers

Figure 4:
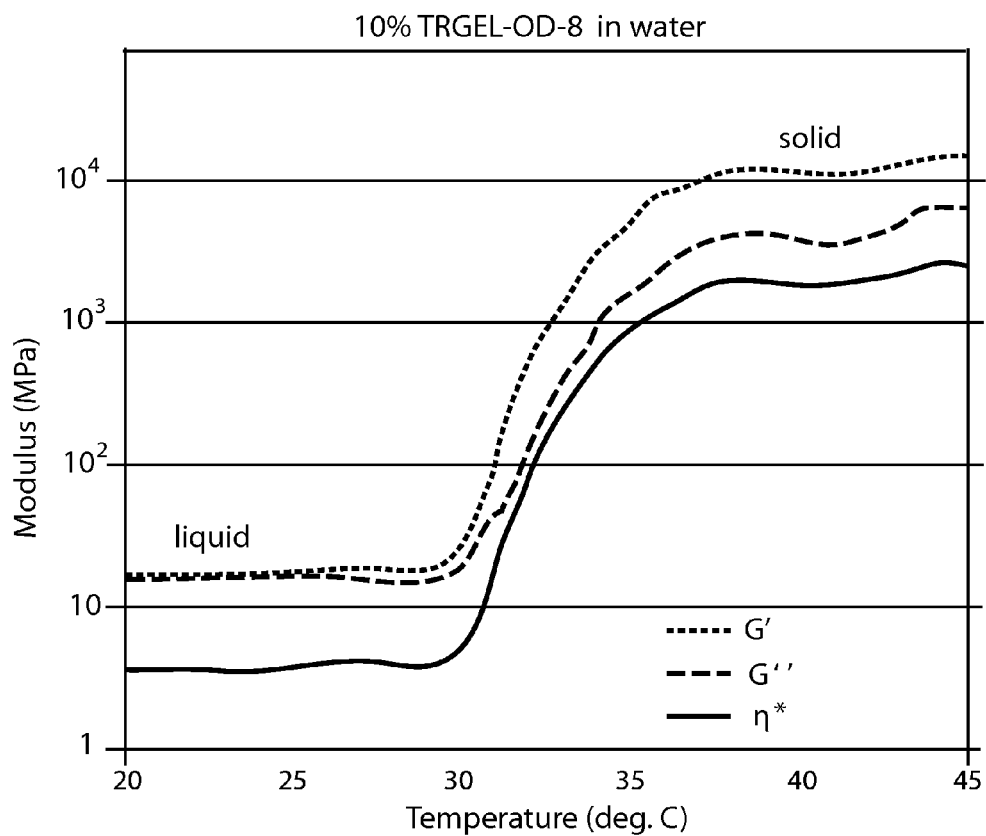
FIG. 4 presents a graph showing the viscoelastic transitions of an RTG polymer of the present invention.
Figure 5:
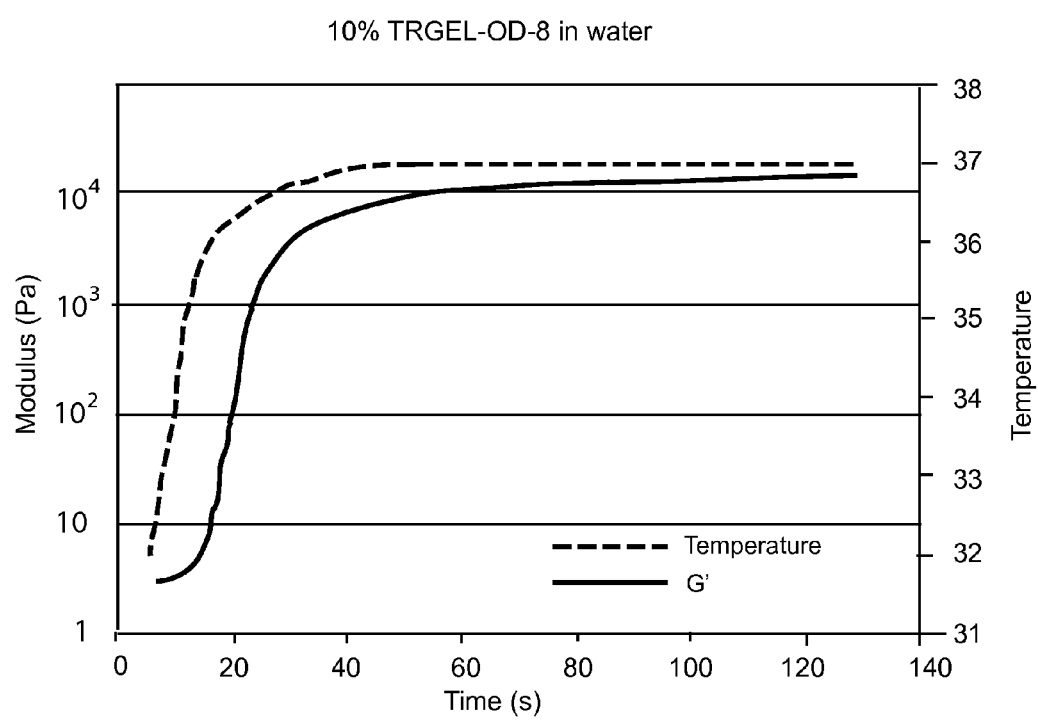
FIG. 5 presents a graph of the solution kinetics of the RTG polymer of FIG. 4.

To determine gelation temperature, water-soluble polymers of the present invention were dissolved in water at 10% w/v and solution temperature was increases at approximately 2° C./min as the viscosity of the solution was monitored with rheometer (TA Instruments, model number AR-62). The lowest temperature at which the solution ceased to flow was recorded as the gelation temperature. Gelation temperatures of representative water-soluble carbohydrate polyethers of the present invention as determined by the procedure described herein are presented in Table 5 and a graph showing the gelation temperature (Gel Point) vs. Mol % DGDM in MDM/DGDM copolymers is presented in FIG. 3. A graph showing the viscoelastic transitions of a 10% aqueous solution of the polymer designated as TRGEL-OD-8 in Table 5 is shown in FIG. 4, while a graphic presentation of the solution kinetics is shown in FIG. 5. For water-soluble homopolymers comprising monomer units of structural formula (IX), the lowest critical solution temperature point (LCST point) vs. p (number of $CH_2CH_2$—O units in side-chain) is presented in Table 6.

TABLE 6

| Polymer Designation | p= | LCST (° C.) |
|---|---|---|
| poly-MDM | 0 | n/a |
| poly-MDM | 1 | 30 |
| poly-DGDM | 2 | 54 |
| poly-3GDM | 3 | 74 |

Example 26

Human mesenchymal stem cells were incubated in a p-MDM/DGDM thermally reversible gel both before and after gelation at 37° C. Thermally activated capture and release of cells was carried on for one week after which time the cells were replated and showed viability and capacity to grow.

Example 27

Figure 6:
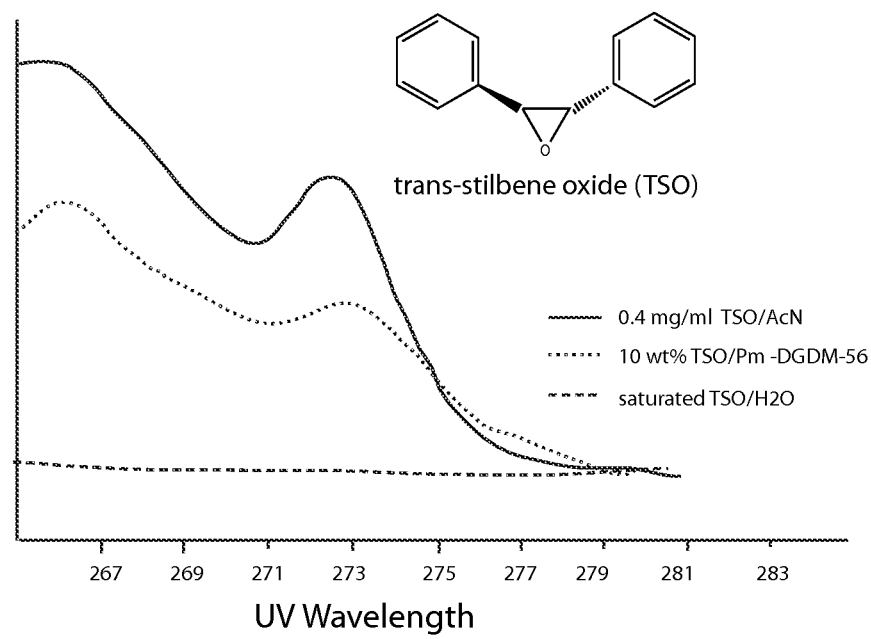
FIG. 6 is a graphic presentation of the solubility of trans-stilbene oxide in an aqueous solution containing of p-MDM/DGDM copolymer.

Solutions of trans-stilbene oxide were prepared in water and in a 10% solution of p-MDM/DGDM copolymer. The UV spectra of the solutions are presented in FIG. 6 reveals that solubility hydrophobic trans-stilbene oxide in the 10% solution of p-MDM/DGDM copolymer was improved over the solubility in water.

Example 28

In Table 7 it is shown that in vivo gel residence time of polymers of the present invention is controlled by adjusting polymer MW, side group structure, polymer concentration as well as by opening of the 1,6-anhydro rings. In vivo gel degradation/dissolution/assimilation time is controlled by these means from a few days to one year or more.

TABLE 7

| Control | Range | Transition Temp | Modulus | Release Kinetics |
|---|---|---|---|---|
| MW | 2.5-130 kDa | — | ↑ | ↓ |
| Hydrophobic Component | 50-80 wt % | ↓ | ↑ | ↓ |
| Concentration | >3 wt % | — | ↑ | ↓ |
| Low MW additive | 0.9 wt % NaCl | ↓ | ↑ | ↑ |
| Acetylation | ~1% | — | — | ↑ |

Example 29

A 10% solution of p-MDM/DGDM was dropped into water at 37° C. wherein a thermally reversible hydrogel was immediately formed.

Example 30

In Vivo Resorption of TRGel Polymers in Mice

A 10% solution of a random t-MDM/MEDM/DGDM terpolymer (monomer ratio of 59/20/21 mol %) in PBS buffer was cold sterilized by filtration and 200 μL doses were injected subcutaneously in mice. A polymer depot was immediately formed under the skin and depot size was monitored as a function of time. Resorption of the polymer was monitored and results are presented in Table 8 TableComplete resorption of the polymer was observed in app 100 days.

TABLE 8

| day | Depot size (%) animal 1 | Depot size (%) animal 2 |
|---|---|---|
| 0 | 100 | 100 |
| 7 | 95 | 100 |
| 21 | 86 | 84 |
| 30 | 83 | 79 |
| 50 | 69 | 75 |
| 56 | 66 | 59 |
| 76 | 38 | 21 |

Example 31

Evolution of Gel Point for Random TRGel Terpolymers Blends in PBS

To demonstrate that desired gel transition temperatures can be controlled by utilizing blends of TRGel polymers, two random terpolymers (shown in Table 9) were mixed at variable ratios and dissolved in PBS (10% w/w at 4° C. The gel transition temperature was measured and results are presented in Table 10 and approximated by linear regression, FIG. 1.

TABLE 9

Composition of Polymers

| Monomer (mol %) | Monomer composition MDM | MEDM | DGDM |
|---|---|---|---|
| Polymer ID t-104 | 50 | 25.2 | 24.8 |
| Polymer ID t-120.1 | 57.4 | 5 | 37.6 |

TABLE 10

Evolution of Gel Point for Polymer Blends

| t-104 wt % | t-120.1 wt % | Tgel ° C. |
|---|---|---|
| 0% | 100% | 35 |
| 28% | 72.0% | 34 |
| 49% | 51.2% | 32.5 |
| 73% | 27.2% | 31.5 |
| 100% | 0.0% | 30.5 |

Example 32

Expansion of Gel Point Range Using Block Copolymers

Four co-polymers of monomers MDM and DGDM were prepared with the same total monomer composition of MDM/DGDM monomer 63/37 mol % (+/−3.1%) at 55° C. One polymer was a random copolymer of the MDM/DGDM=63/37 mol % with all monomers added at the same time. Three other polymers were made by sequential addition of monomer pairs as blocks, separated by 3 hr. time intervals. Each block was a random copolymer with composition presented in Table 11. In this manner AB diblock, and ABA and BAB triblocks were prepared. Gel temperature was measured of 10% solutions in PBS and results are summarized in Table 12. In this example Block A was considered hydrophilic and B ass hydrophobic. The data presented in Table 12 demonstrates that the utilization of block polymers extended gel temperature range from 33° C. to 5° C.

TABLE 11

Composition of Blocks and Average Monomer Content.

| Block ID | Monomer MDM (mol %) | Monomer DGDM (mol %) |
|---|---|---|
| A | 55 | 45 |
| B | 70 | 30 |
| Total monomer | 63 | 37 |

TABLE 12

Gel points for 10% Polymer Solutions in PBS

| Polymer ID | Composition | Tgel ° C. |
|---|---|---|
| t-116 | AB | 5.0 |
| t-117 | BAB | 14.5 |
| t-118 | ABA | 28.5 |
| t-118.1 | random | 33.0 |

The invention being thus described, it will be obvious that the same may be varied in many ways. Such variations are not to be regarded as a departure from the spirit and scope of the invention and all such modifications are intended to be included within the scope of the following claims.

We claim:

1. A biomedically useful composition comprising:
   a bioactive agent; and
   a C2-C3 linked polyether of a 1,6:2,3-dianhydrohexopyranose derivative comprising one or more monomeric units selected from the group consisting of a monomeric unit of the structural formula

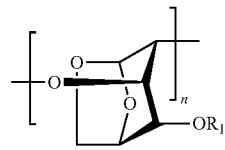

a monomeric unit of the structural formula

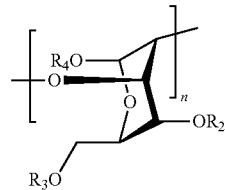

and a monomeric unit of the structural formula

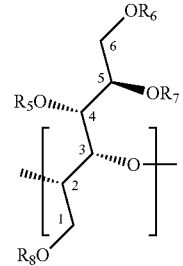

wherein $R_1$, $R_2$, $R_3$, $R_4$, $R_5$, $R_6$, $R_7$ and $R_8$ are moieties chosen such that the polymer composition exhibits reverse thermal gelation properties in aqueous media.

2. The composition of claim 1 wherein at least one of moieties $R_1$, $R_2$, $R_3$, $R_4$, $R_5$, $R_6$, $R_7$ and $R_8$ has the structure:

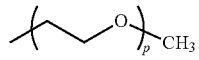

wherein p=an integer from 1 to 10.

3. The composition of claim 2 wherein p is an integer from 1 to 4.

4. The composition of claim 2 wherein p is an integer from 1 to 2.

5. The composition of claim 1 wherein one or more of moieties $R_1$, $R_2$, $R_3$, $R_4$, $R_5$, $R_6$, $R_7$ and $R_8$=OH.

6. The composition of claim 1 with a critical solution temperature from 5° to 74° C.

7. The composition of claim 1 with a critical solution temperature from 5° to 44° C.

8. The polymer composition of claim 1 with a molecular weight from 2 to 350 kDa.

9. The polymer composition of claim 1 with a polydispersity index less than or equal to 1.5.

10. A composition of claim 1 useful as physiologic lubricant.

11. A composition of claim 1 useful for augmentation of body tissue in surgical procedures.

12. A composition of claim 1 useful as biological scaffold in wound healing applications.

13. A composition of claim 1 useful for encapsulation of mammalian cells.

14. A composition of claim 13 wherein the mammalian cells are select from the group consisting of stem cells, islets cells, fibroblast cells, T-cells, B-cells, dendritic cells, osteoblasts, adipose cells, neuronal cells, epithelial cells, smooth muscle sells and liver cells.

15. The composition of claim 1 wherein the bioactive agent is chosen from the group consisting of receptors, hormones, cytokines, hematopoietic factors, growth factors, anti-obesity factors, trophic factors, anti-inflammatory factors, small molecule drugs, nucleic acids, polypeptides and enzymes.

16. The composition of claim 1 wherein the bioactive agent comprises at least one small molecule drug.

17. The composition of claim 16 wherein the small molecule drug is chosen from the group consisting of antibiotics, antivirals, antifungals, antineoplastics, antigeogenics, antiarrhythmics, anticoagulants, antihistamines, antihypertensives, antipsychotics, sedatives, contraceptives, decongestants, diuretics, and immunosurpressants.

18. The composition of claim 15 wherein the bioactive agent is a polypeptide.

19. The composition of claim 18 wherein the polypeptide is selected from the group consisting of oxytocin, vasopressin, adrenocorticotropic hormone, epidermal growth factor, platelet-derived growth factor, prolactin, luliberin, growth hormone, growth hormone releasing factor, insulin, somatostatin, glucagon, interleukin-2, interferon-$\alpha$, interferon-$\beta$, interferon-$\gamma$, gastrin, tetragastrin, pentagastrin, urogastrone, secretin, calcitonin, enkephalins, endorphins, angiotensins, thyrotropin releasing hormone, tumor necrosis factor, nerve growth factor, granulocyte-colony stimulating factor, granulocyte macrophage-colony stimulating factor, macrophage-colony stimulating factor, heparinase, bone morphogenic protein, hANP, glucagon-like peptide, interleukin-11, renin, bradykinin, bacitracins, polymyxins, colistins, tyrocidine, gramicidins, cyclosporins, enzymes, cytokines, monoclonal antibodies and vaccines.

20. The composition of claim 1 wherein the bioactive agent is a selected from the group consisting of salts and buffers.

21. The composition of claim 20 wherein the biomedically useful composition is effective in removing wrinkles on human skin.

* * * * *